US012215373B1

(12) United States Patent
Liu et al.

(10) Patent No.: US 12,215,373 B1
(45) Date of Patent: Feb. 4, 2025

(54) MODIFIED YEAST MICROORGANISMS TO INCREASE YIELD OF 3-HYDROPROPIONIC ACID

(71) Applicant: National Technology & Engineering Solutions of Sandia, LLC, Albuquerque, NM (US)

(72) Inventors: Di Liu, Emeryville, CA (US); Peter Britton Otoupal, Oakland, CA (US); HeeJin Hwang, Emeryville, CA (US); John Michael Gladden, Martinez, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 52 days.

(21) Appl. No.: 18/121,697

(22) Filed: Mar. 15, 2023

(51) Int. Cl.
C12P 7/52 (2006.01)
C12N 1/20 (2006.01)
C12N 9/22 (2006.01)

(52) U.S. Cl.
CPC ................ *C12P 7/52* (2013.01); *C12N 1/205* (2021.05); *C12N 9/22* (2013.01); *C12N 2310/20* (2017.05)

(58) Field of Classification Search
None
See application file for complete search history.

(56) References Cited

U.S. PATENT DOCUMENTS

2018/0148744 A1* 5/2018 Knight .................... C12N 15/52

FOREIGN PATENT DOCUMENTS

CN 114317388 A * 4/2022

OTHER PUBLICATIONS

Coradetti, Samuel T., et al. "Functional genomics of lipid metabolism in the oleaginous yeast Rhodosporidium toruloides." Elife 7 (2018): e32110 (Year: 2018).*
Pomraning, Kyle R.; "Integration of Proteomics and Metabolomics Into the Design, Build, Test, Learn Cycle to Improve 3-Hydroxypropionic Acid Production in Aspergillus pseudoterreus", frontiers in Bioengineering and Biotechnology, Original Research, published: Apr. 7, 2021, doi: 10.3389/fbioe.2021.603832, 12 pages.
Liu, C. et al. "Functional balance between enzymes in malonyl-CoA pathway for 3-hydroxypropionate biosynthesis", Metabolic Engineering (2016) 34:104-111.
Nguyen-Vo, T. P. et al., "Systems evaluation reveals novel transporter YohJK renders 3-hydroxypropionate tolerance in *Escherichia coli*", Scientific Reports (2020) 10:19064, 12 pages.

Ageitos, J.M., Vallejo, J.A., Veiga-Crespo, P., Villa, T.G., 2011. Oily yeasts as oleaginous cell factories. Appl Microbiol Biotechnol 90, 1219-1227. https://doi.org/10.1007/s00253-011-3200-z.
Arenas-López, C., Locker, J., Orol, D., Walter, F., Busche, T., Kalinowski, J., Minton, N.P., Kovács, K., Winzer, K., 2019. The genetic basis of 3-hydroxypropanoate metabolism in Cupriavidus necator H16. Biotechnol Biofuels 12, 150. https://doi.org/10.1186/s13068-019-1489-5.
Beerthuis, R., Rothenberg, G., Shiju, N.R., 2015. Catalytic routes towards acrylic acid, adipic acid and E-caprolactam starting from biorenewables. Green Chemistry 17, 1341-1361. https://doi.org/10.1039/C4GC02076F.
Borodina, I., Kildegaard, K.R., Jensen, N.B., Blicher, T.H., Maury, J., Sherstyk, S., Schneider, K., Lamosa, P., Herrgård, M.J., Rosenstand, I., Öberg, F., Forster, J., Nielsen, J., 2015. Establishing a synthetic pathway for high-level production of 3-hydroxypropionic acid in Saccharomyces cerevisiae via ß-alanine. Metab Eng 27, 57-64. https://doi.org/10.1016/j.ymben.2014.10.003.
Casal, M., Paiva, S., Queirós, O., Soares-Silva, I., 2008. Transport of carboxylic acids in yeasts. FEMS Microbiol Rev 32, 974-994. https://doi.org/10.1111/j.1574-6976.2008.00128.x.
Chen, X., Kuhn, E., Jennings, E.W., Nelson, R., Tao, L., Zhang, M., Tucker, M.P., 2016. DMR (deacetylation and mechanical refining) processing of corn stover achieves high monomeric sugar concentrations (230 g L -1 ) during enzymatic hydrolysis and high ethanol concentrations (>10% v/v) during fermentation without hydrolysate purification or concentration. Energy Environ Sci 9, 1237-1245. https://doi.org/10.1039/C5EE03718B.
Chen, Y., Bao, J., Kim, I.-K., Siewers, V., Nielsen, J., 2014. Coupled incremental precursor and co-factor supply improves 3-hydroxypropionic acid production in Saccharomyces cerevisiae. Metab Eng 22, 104-109. https://doi.org/10.1016/j.ymben.2014.01.005.
Cheng, Z., Jiang, J., Wu, H., Li, Z., Ye, Q., 2016. Enhanced production of 3-hydroxypropionic acid from glucose via malonyl-CoA pathway by engineered Escherichia coli. Bioresour Technol 200, 897-904. https://doi.org/10.1016/j.biortech.2015.10.107.
Coradetti, S., Pinel, D., Geiselman, G., Ito, M., Mondo, S., Reilly, M., Cheng, Y.-F., Bauer, S., Grigoriev, I., Gladden, J., Simmons, B., Brem, R., Arkin, A., Skerker, J., 2017. Functional genomics of lipid metabolism in the oleaginous yeast Rhodosporidium toruloides. eLife 32110, https://doi.org 10.7554/eLife.32110.
Coradetti, S.T., Pinel, D., Geiselman, G.M., Ito, M., Mondo, S.J., Reilly, M.C., Cheng, Y.-F., Bauer, S., Grigoriev, I. v, Gladden, J.M., Simmons, B.A., Brem, R.B., Arkin, A.P., Skerker, J.M., 2018. Functional genomics of lipid metabolism in the oleaginous yeast Rhodosporidium toruloides. Elife 7. https://doi.org/10.7554/eLife.32110.

(Continued)

*Primary Examiner* — Paul J Holland
*Assistant Examiner* — Erica Nicole Jones-Foster
(74) *Attorney, Agent, or Firm* — Eschweiler & Potashnik, LLC; Samantha Updegraff

(57) ABSTRACT

Methods and compositions (e.g., engineered hosts) are disclosed for use in converting biomass to 3-hydropropionic acid. In particular embodiments, the methods include use of an engineered *Rhodosporidium* yeast, such as *R. toruloides*, the engineered *R. toruloides* having the RT04_8975 gene deleted from its genome, combined with a lignocellulosic hydrolysate, sourced, for example, from a biomass. A promoter for enhancing transport of 3HP is also incorporated by addition to the *R. toruloides* genome, for example, by modified lithium acetate transformation.

17 Claims, 26 Drawing Sheets
Specification includes a Sequence Listing.

(56) References Cited

OTHER PUBLICATIONS

Das, L., Geiselman, G.M., Rodriguez, A., Magurudeniya, H.D., Kirby, J., Simmons, B.A., Gladden, J.M., 2021. Seawater-based one-pot ionic liquid pretreatment of sorghum for jet fuel production. Bioresour Technol Rep 13, 100622. https://doi.org/10.1016/j.biteb.2020.100622.

Della Pina, C., Falletta, E., Rossi, M., 2011. A green approach to chemical building blocks. The case of 3-hydroxypropanoic acid. Green Chemistry 13, 1624. https://doi.org/10.1039/c1gc15052a.

Evans, C.T., Ratledge, C., 1984. Influence of Nitrogen Metabolism on Lipid Accumulation by Rhodosporidium toruloides CBS 14. Journal of Microbiology (N Y) 130, 1705-1710. https://doi.org/10.1099/00221287-130-7-1705.

Fillet, S., Adrio, J.L., 2016. Microbial production of fatty alcohols. World J Microbiol Biotechnol 32, 152. https://doi.org/10.1007/s11274-016-2099-z.

Geiselman, G.M., Kirby, J., Landera, A., Otoupal, P., Papa, G., Barcelos, C., Sundstrom, E.R., Das, L., Magurudeniya, H.D., Wehrs, M., Rodriguez, A., Simmons, B.A., Magnuson, J.K., Mukhopadhyay, A., Lee, T.S., George, A., Gladden, J.M., 2020a. Conversion of poplar biomass into high-energy density tricyclic sesquiterpene jet fuel blendstocks. Microb Cell Fact 19, 208. https://doi.org/10.1186/s12934-020-01456-4.

Geiselman, G.M., Zhuang, X., Kirby, J., Tran-Gyamfi, M.B., Prahl, J.-P., Sundstrom, E.R., Gao, Y., Munoz Munoz, N., Nicora, C.D., Clay, D.M., Papa, G., Burnum-Johnson, K.E., Magnuson, J.K., Tanjore, D., Skerker, J.M., Gladden, J.M., 2020b. Production of ent-kaurene from lignocellulosic hydrolysate in Rhodosporidium toruloides. Microb Cell Fact 19, 24. https://doi.org/10.1186/s12934-020-1293-8.

Ham, T.S., Dmytriv, Z., Plahar, H., Chen, J., Hillson, N.J., Keasling, J.D., 2012. Design, implementation and practice of JBEI-ICE: an open source biological part registry platform and tools. Nucleic Acids Res 40, e141-e141. https://doi.org/10.1093/nar/gks531.

Hu, C., Zhao, X., Zhao, J., Wu, S., Zhao, Z.K., 2009. Effects of biomass hydrolysis by-products on oleaginous yeast Rhodosporidium toruloides. Bioresour Technol 100, 4843-4847. https://doi.org/10.1016/j.biortech.2009.04.041.

Hügler, M., Menendez, C., Schägger, H., Fuchs, G., 2002. Malonyl-Coenzyme A Reductase from Chloroflexus aurantiacus, a Key Enzyme of the 3-Hydroxypropionate Cycle for Autotrophic CO 2 Fixation. J Bacteriol 184, 2404-2410. https://doi.org/10.1128/JB.184.9.2404-2410.2002.

Ji, R.-Y., Ding, Y., Shi, T.-Q., Lin, L., Huang, H., Gao, Z., Ji, X.-J., 2018. Metabolic Engineering of Yeast for the Production of 3-Hydroxypropionic Acid. Front Microbiol 9. https://doi.org/10.3389/fmicb.2018.02185.

Jiang, J., Huang, B., Wu, H., Li, Z., Ye, Q., 2018. Efficient 3-hydroxypropionic acid production from glycerol by metabolically engineered Klebsiella pneumoniae. Bioresour Bioprocess 5, 34. https://doi.org/10.1186/s40643-018-0218-4.

Jiao, X., Zhang, Y., Liu, X., Zhang, Q., Zhang, S., Zhao, Z.K., 2019. Developing a CRISPR/Cas9 System for Genome Editing in the Basidiomycetous Yeast Rhodosporidium toruloides. Biotechnol J 14, 1900036. https://doi.org/10.1002/biot.201900036.

Kildegaard, K.R., Wang, Z., Chen, Y., Nielsen, J., Borodina, I., 2015. Production of 3-hydroxypropionic acid from glucose and xylose by metabolically engineered Saccharomyces cerevisiae. Metab Eng Commun 2, 132-136. https://doi.org/10.1016/j.meteno.2015.10.001.

Kim, Jinho, Baidoo, E.E.K., Amer, B., Mukhopadhyay, A., Adams, P.D., Simmons, B.A., Lee, T.S., 2021. Engineering Saccharomyces cerevisiae for isoprenol production. Metab Eng 64, 154-166. https://doi.org/10.1016/j.ymben.2021.02.002.

Kim, Joonhoon, Coradetti, S.T., Kim, Y.-M., Gao, Y., Yaegashi, J., Zucker, J.D., Munoz, N., Zink, E.M., Burnum-Johnson, K.E., Baker, S.E., Simmons, B.A., Skerker, J.M., Gladden, J.M., Magnuson, J.K., 2021. Multi-Omics Driven Metabolic Network Reconstruction and Analysis of Lignocellulosic Carbon Utilization in Rhodosporidium toruloides. Front Bioeng Biotechnol 8. https://doi.org/10.3389/fbioe.2020.612832.

Kirby, J., Geiselman, G.M., Yaegashi, J., Kim, J., Zhuang, X., Tran-Gyamfi, M.B., Prahl, J.-P., Sundstrom, E.R., Gao, Y., Munoz, N., Burnum-Johnson, K.E., Benites, V.T., Baidoo, E.E.K., Fuhrmann, A., Seibel, K., Webb-Robertson, B.-J. M., Zucker, J., Nicora, C.D., Tanjore, D., Magnuson, J.K., Skerker, J.M., Gladden, J.M., 2021. Further engineering of R. toruloides for the production of terpenes from lignocellulosic biomass. Biotechnol Biofuels 14, 101. https://doi.org/10.1186/s13068-021-01950-w.

Kumar, V., Ashok, S., Park, S., 2013. Recent advances in biological production of 3-hydroxypropionic acid. Biotechnol Adv 31, 945-961. https://doi.org/10.1016/j.biotechadv.2013.02.008.

Lama, S., Kim, Y., Nguyen, D.T., Im, C.H., Sankaranarayanan, M., Park, S., 2021. Production of 3-hydroxypropionic acid from acetate using metabolically-engineered and glucose-grown Escherichia coli. Bioresour Technol 320, 124362. https://doi.org/10.1016/j.biortech.2020.124362.

Lee, J.J.L., Ng, K.R., Liang, J., Cui, X., Li, A., Chen, W.N., 2022. Engineering the Phenylpropanoid Pathway in Rhodosporidium toruloides for Naringenin Production from Tyrosine by Leveraging on its Native PAL Gene. ACS Food Science & Technology. https://doi.org/10.1021/acsfoodscitech.2c00301.

Li, Y., Liu, B., Zhao, Z., Bai, F., 2006. Optimization of Culture Conditions for Lipid Production by Rhodosporidium toruloides. Chin J Biotechnol 22, 650-656. https://doi.org/10.1016/S1872-2075(06)60050-2.

Li, Y., Wang, X., Ge, X., Tian, P., 2016. High Production of 3-Hydroxypropionic Acid in Klebsiella pneumoniae by Systematic Optimization of Glycerol Metabolism. Sci Rep 6, 26932. https://doi.org/10.1038/srep26932.

Lin, C-Y et al., Evaluation of engineered low-lignin poplar for conversion into advanced biproducts. 2022. Biotechnology for Biofules and Bioproducts. https://doi.org/10.1186/s13068-022-02245-4.

Liu, C., Ding, Y., Zhang, R., Liu, H., Xian, M., Zhao, G., 2016. Functional balance between enzymes in malonyl-CoA pathway for 3-hydroxypropionate biosynthesis. Metab Eng 34, 104-111. https://doi.org/10.1016/j.ymben.2016.01.001.

Liu, C., Wang, Q., Xian, M., Ding, Y., Zhao, G., 2013. Dissection of Malonyl-Coenzyme A Reductase of Chloroflexus aurantiacus Results in Enzyme Activity Improvement. PLoS One 8, e75554. https://doi.org/10.1371/journal.pone.0075554.

Liu, D., Geiselman, G.M., Coradetti, S., Cheng, Y., Kirby, J., Prahl, J., Jacobson, O., Sundstrom, E.R., Tanjore, D., Skerker, J.M., Gladden, J., 2020. Exploiting nonionic surfactants to enhance fatty alcohol production in Rhodosporidium toruloides. Biotechnol Bioeng 117, 1418-1425. https://doi.org/10.1002/bit.27285.

Liu, D., Xiao, Y., Evans, B.S., Zhang, F., 2015. Negative Feedback Regulation of Fatty Acid Production Based on a Malonyl-CoA Sensor-Actuator. ACS Synth Biol 4, 132-140. https://doi.org/10.1021/sb400158w.

Liu, H., Zhao, X., Wang, F., Li, Y., Jiang, X., Ye, M., Zhao, Z.K., Zou, H., 2009. Comparative proteomic analysis of Rhodosporidium toruloides during lipid accumulation. Yeast 26, 553-566. https://doi.org/10.1002/yea.1706.

Love, M.I., Huber, W., Anders, S., 2014. Moderated estimation of fold change and dispersion for RNA-seq data with DESeq2. Genome Biol 15. https://doi.org/10.1186/s13059-014-0550-8.

Nguyen, N.H., Kim, J.-R., Park, S., 2019. Development of Biosensor for 3-Hydroxypropionic Acid. Biotechnology and Bioprocess Engineering 24, 109-118. https://doi.org/10.1007/s12257-018-0380-8.

Nguyen-Vo, T.P., Ko, S., Ryu, H., Kim, J.R., Kim, D., Park, S., 2020. Systems evaluation reveals novel transporter YohJK renders 3-hydroxypropionate tolerance in Escherichia coli. Sci Rep 10, 19064. https://doi.org/10.1038/s41598-020-76120-3.

Nguyen-Vo, T.P., Ryu, H., Sauer, M., Park, S., 2022. Improvement of 3-hydroxypropionic acid tolerance in Klebsiella pneumoniae by novel transporter YohJK. Bioresour Technol 346, 126613. https://doi.org/10.1016/j.biortech.2021.126613.

(56) References Cited

OTHER PUBLICATIONS

Nora, L.C., Wehrs, M., Kim, J., Cheng, J.-F., Tarver, A., Simmons, B.A., Magnuson, J., Harmon-Smith, M., Silva- Rocha, R., Gladden, J.M., Mukhopadhyay, A., Skerker, J.M., Kirby, J., 2019. A toolset of constitutive promoters for metabolic engineering of Rhodosporidium toruloides. Microb Cell Fact 18, 117. https://doi.org/10.1186/s12934-019-1167-0.

Osorio-González, C.S., Hegde, K., Ferreira, P., Brar, S.K., Kermanshahipour, A., Soccol, C.R., Avalos-Ramírez, A., 2019. Lipid production in Rhodosporidium toruloides using C-6 and C-5 wood hydrolysate: A comparative study. Biomass Bioenergy 130, 105355. https://doi.org/10.1016/j.biombioe.2019.105355.

Otoupal, P.B., Ito, M., Arkin, A.P., Magnuson, J.K., Gladden, J.M., Skerker, J.M., 2019. Multiplexed CRISPR-Cas9-Based Genome Editing of Rhodosporidium toruloides. mSphere 4. https://doi.org/10.1128/mSphere.00099-19.

Park, Y.-K., Nicaud, J.-M., Ledesma-Amaro, R., 2018. The Engineering Potential of Rhodosporidium toruloides as a Workhorse for Biotechnological Applications. Trends Biotechnol 36, 304-317. https://doi.org/10.1016/j.tibtech.2017.10.013.

Pomraning, K.R., Dai, Z., Munoz, N., Kim, Y.-M., Gao, Y., Deng, S., Kim, J., Hofstad, B.A., Swita, M.S., Lemmon, T., Collett, J.R., Panisko, E.A., Webb-Robertson, B.-J.M., Zucker, J.D., Nicora, C.D., de Paoli, H., Baker, S.E., Burnum-Johnson, K.E., Hillson, N.J., Magnuson, J.K., 2021. Integration of Proteomics and Metabolomics Into the Design, Build, Test, Learn Cycle to Improve 3-Hydroxypropionic Acid Production in Aspergillus pseudoterreus. Front Bioeng Biotechnol 9. https://doi.org/10.3389/fbioe.2021.603832.

Pomraning, K.R., Dai, Z., Munoz, N., Kim, Y.M., Gao, Y., Deng, S., Lemmon, T., Swita, M.S., Zucker, J.D., Kim, J., Mondo, S.J., Panisko, E., Burnet, M.C., Webb-Robertson, B.J.M., Hofstad, B., Baker, S.E., Burnum-Johnson, K.E., Magnuson, J.K., 2022. Itaconic acid production is regulated by LaeA in Aspergillus pseudoterreus. Metab Eng Commun 15. https://doi.org/10.1016/j.mec.2022.e00203.

Qiao, K., Imam Abidi, S.H., Liu, H., Zhang, H., Chakraborty, S., Watson, N., Kumaran Ajikumar, P., Stephanopoulos, G., 2015. Engineering lipid overproduction in the oleaginous yeast Yarrowia lipolytica. Metab Eng 29, 56-65. https://doi.org/10.1016/j.ymben.2015.02.005.

Rathnasingh, C., Raj, S.M., Lee, Y., Catherine, C., Ashok, S., Park, S., 2012. Production of 3-hydroxypropionic acid via malonyl-CoA pathway using recombinant Escherichia coli strains. J Biotechnol 157, 633-640. https://doi.org/10.1016/j.jbiotec.2011.06.008.

Riscaldati, E., Moresi, M., Federici, F., Petruccioli, M., 2000. Effect of pH and stirring rate on itaconate production by Aspergillus terreus, Journal of Biotechnology.

\* cited by examiner

Reductive pathway

Oxidative pathway

SEQ ID NO: 1

RT04_8975

MLSHTLRTSGSLRTLATRRTFTTTPARRALADLEALAATHPWSGTATDGQRATTHLIGGEYTTG
DSTHWIDVHDPSTQRVLTRVPESTPQVLKRAVDKAEEAFDEWKDSSILKRQAVMLKFQSLIREH
HDEIARSIVLEQGKTFADAKGDVLRGLQVVENACGIPSLLLADKLEVSKDMDTFVRKVPLGVTA
AVCPFNFPAMIPLWAMGMSIACGNSLILKPSERDPGATMILAELLEQAGLPKGVLQVVHGTIAPV
KFICEEPRIKAISFVGGDKAGQYIYETGSKNGKRVQANLGAKNHCILMPDANANFALNSIVGAAF
GAAGQRCMALSTLVAVGESQTWIDGLVERAKKLKVGNGFDPETEVGPLITPAAKERVESLIQSC
ADQGGKILLDGRGAKPKGYEKGNFVGPTILEATTDMDCYTQEIFGPVLTIVKADTLDDAIALINR
NRYGNGSSVFTNSGATARRFEKEIQAGQVGINVPIPVPLPMFSWSGNKGSVLGGASLYGPRGVDF
WTQNKTVTSYWRAEDAIDTRATTAMPTHH

SEQ ID NO: 2

*MCR<sub>CA</sub>-NTERM:*
*ATGTCGGGCACGGGCCGCCTCGCGGGCAAGATCGCGCTCATCACGGGCGGCGCGGGCAACATC*
*GGCTCGGAGCTCACGCGCCGCTTCCTCGCGGAGGGCGCGACGGTCATCATCTCGGGCCGCAACC*
*GCGCGAAGCTCACGGCGCTCGCGGAGCGCATGCAGGCGGAGGCGGGCGTCCCGGCGAAGCGC*
*ATCGACCTCGAGGTCATGGACGGCTCGGACCCGGTCGCGGTCCGCGCGGGCATCGAGGCGATC*
*GTCGCGCGCCACGGCCAGATCGACATCCTCGTCAACAACGCGGGCTCGGCGGGCGCGCAGCGC*
*CGCCTCGCGGAGATCCCGCTCACGGAGGCGGAGCTCGGCCCGGGCGCGGAGGAGACGCTCCAC*
*GCGTCGATCGCGAACCTCCTCGGCATGGGCTGGCACCTCATGCGCATCGCGGCGCCGCACATGC*
*CGGTCGGCTCGGCGGTCATCAACGTCTCGACGATCTTCTCGCGCGGAGTACTACGGCCGCATC*
*CCGTACGTCACGCCGAAGGCGGCGCTCAACGCGCTCTCGCAGCTCGCGGCGCGAGCTCGGC*
*GCGCGCGGCATCCGCGTCAACACGATCTTCCCGGGCCCGATCGAGTCGGACCGCATCCGCACGG*
*TCTTCCAGCGCATGGACCAGCTCAAGGGCCGCCCGGAGGGCGACACGGCGCACCACTTCCTCAA*
*CACGATGCGCCTCTGCCGCGCGAACGACCAGGGCGCGCTCGAGCGCCGCTTCCCGTCGGTCGG*
*CGACGTCGCGGACGCGGCGGTCTTCCTCGCGTCGGCGGAGTCGGCGGCGCTCTCGGGCGAGAC*
*GATCGAGGTCACGCACGGCATGGAGCTCCGGCGTGCTCGGAGACGTCGCTCCTCGCGCGCACG*
*GACCTCCGCACGATCGACGCGTCGGGCCGCACGACGCTCATCTGCGCGGGCGACCAGATCGAGG*
*AGGTCATGGCGCTCACGGGCATGCTCCGCACGTGCGGCTCGGAGGTCATCATCGGCTTCCGCTC*
*GGCGGCGGCGCTCGCGCAGTTCGAGCAGGCGGTCAACGAGTCGCGCCGCCTCGCGGGCGCGGA*
*CTTCACGCCGCCGATCGCGCTCCCGCTCGACCCGCGCGACCCGGCGACGATCGACGCGGTCTTC*
*GACTGGGCGGGCGAGAACACGGGCGGCATCCACGCGGCGGTCATCCTCCCGGCGACGTCGCAC*
*GAGCCGGCGCCGTGCGTCATCGAGGTCGACGACGAGCGCGTCCTCAACTTCCTCGCGGACGAGA*
*TCACGGGCACGATCGTCATCGCGTCGCGCCTCGCGCGCTACTGGCAGTCGCAGCGCCTCACGCC*
*GGGCGCGCGCGCGCGGCCCGCGCGTCATCTTCCTCTCGAACGGCGCGGACCAGAACGGCAA*
*CGTCTACGGCCGCATCCAGTCGGCGGCGATCGGCCAGCTCATCCGCGTCTGGCGCCACGAGGCG*
*GAGCTCGACTACCAGCGCGCGTCGGCGGCGGGCGACCACGTCCTCCCGCCGGTCTGGGCGAAC*
*CAGATCGTCCGCTTCGCGAACCGCTCGCTCGAGGGCCTCGAGTTCGCGTGCGCGTGGACGGCGC*
*AGCTCCTCCACTCGCAGCGCCACATCAACGAGATCACGCTCAACATCCCGGCGAACATCTAA*

FIG. 20

SEQ ID NO: 3

*MCR<sub>CA</sub>-CTERM:*

*ATGTCGGCGACGACGGGCGCGCGCTCGGCGTCGGTCGGCTGGGCGGAGTCGCTCATCGGCCTCCAC
CTCGGCAAGGTCGCGCTCATCACGGGCGGCTCGGCGGGCATCGGCGGCCAGATCGGCCGCCTCCTC
GCGCTCTCGGGCGCGCGCGTCATGCTCGCGGCGCGCGACCGCCACAAGCTCGAGCAGATGCAGGCG
ATGATCCAGTCGGAGCTCGCGGAGGTCGGCTACACGGACGTCGAGGACCGCGTCCACATCGCGCCGG
GCTGCGACGTCTCGTCGGAGGCGCAGCTCGCGGACCTCGTCGAGCGCACGCTCTCGGCGTTCGGCAC
GGTCGACTACCTCATCAACAACGCGGGCATCGCGGGCGTCGAGGAGATGGTCATCGACATGCCGGTC
GAGGGCTGGCGCCACACGCTCTTCGCGAACCTCATCTCGAACTACTCGCTCATGCGCAAGCTCGCGCC
GCTCATGAAGAAGCAGGGCTCGGGCTACATCCTCAACGTCTCGTCGTACTTCGGCGGCGAGAAGGACG
CGGCGATCCCGTACCCGAACCGCGCGGACTACGCGGTCTCGAAGGCGGGCCAGCGCGCGATGGCGG
AGGTCTTCGCGCGCTTCCTCGGCCCGGAGATCCAGATCAACGCGATCGCGCCGGGCCCGGTCGAGGG
CGACCGCCTCCGCGGCACGGGCGAGCGCCCGGGCCTCTTCGCGCGCCGCGCGCCTCATCCTCGA
GAACAAGCGCCTCAACGAGCTCCACGCGGCGCTCATCGCGGCGGCGCGCACGGACGAGCGCTCGATG
CACGAGCTCGTCGAGCTCCTCCTCCCGAACGACGTCGCGGCGCTCGAGCAGAACCCGGCGGCGCCGA
CGGCGCTCCGCGAGCTCGCGCGCCGCTTCCGCTCGGAGGGCGACCCGGCGGCGTCGTCGTCGTCGG
CGCTCCTCAACCGCTCGATCGCGGCGAAGCTCCTCGCGCGCCTCCACAACGGCGGCTACGTCCTCCC
GGCGGACATCTTCGCGAACCTCCCCGAACCCGCCGGACCCGTTCTTCACGCGCGCGCAGATCGACCGC
GAGGCGCGCAAGGTCCGCGACGGCATCATGGGCATGCTCTACCTCCAGCGCATGCCGACGGAGTTCG
ACGTCGCGATGGCGACGGTCTACTACCTCGCGGACCGCAACGTCTCGGGCGAGACGTTCCACCCGTC
GGGCGGCCTCCGCTACGAGCGCACGCCGACGGGCGGCGAGCTCTTCGGCCTCCCGTCGCCGGAGCG
CCTCGCGGAGCTCGTCGGCTCGACGGTCTACCTCATCGGCGAGCACCTCACGGAGCACCTCAACCTCC
TCGCGCGCGCGTACCTCGAGCGCTACGGCGCGCGCCAGGTCGTCATGATCGTCGAGACGGAGACGGG
CGCGGAGACGATGCGCCGCCTCCTCCACGACCACGTCGAGGCGGGCCGCCTCATGACGATCGTCGCG
GGCGACCAGATCGAGGCGGCGATCGACCAGGCGATCACGCGCTACGGCCGCCCGGGCCCGGTCGTC
TGCACGCCGTTCCGCCCGCTCCCGACGGTCCCGCTCGTCGGCCGCAAGGACTCGGACTGGTCGACGG
TCCTCTCGGAGGCGGAGTTCGCGGAGCTCTGCGAGCACCAGCTCACGCACCACTTCCGCGTCGCGCG
CAAGATCGCGCTCTCGGACGGCGCGTCGCTCGCGCTCGTCACGCCGGAGACGACGGCGACGTCGACG
ACGGAGCAGTTCGCGCTCGCGAACTTCATCAAGACGACGCTCCACGCGTTCACGGCGACGATCGGCGT
CGAGTCGGAGCGCACGGCGCAGCGCATCCTCATCAACCAGGTCGACCTCACGCGCCGCGCGCGCGC
GGAGGAGCCGCGCGACCCGCACGAGCGCCAGCAGGAGCTCGAGCGCTTCATCGAGGCGGTCCTCCT
CGTCACGGCGCCGCTCCCGCCGGAGGCGGACACGCGCTACGCGGGCCGCATCCACCGCGGCCGCGC
GATCACGGTCTAA*

SEQ ID NO: 4

PROTEIN SEQUENCE OF G2945 (3HP TRANSPORTER):

MPSNTRVASISHGSDFSLSLPPDGGARAWTQVLCMHFVFFNTWGVSNSFSVYQQLYTASFTQSASEIS
WIGSVQVFLLFFIGVLAGRATDAGYFRPVYMAGVLLQLVGIFMLSLCKTYWQVFLAQAVCMGLGNG
LVFTPGLSVMSSYFEKNRAFAVGLAASGAATGGMVYPVVVNQLLYTHSIGFAWTTRAAGLVMLLTH
LPGLVLFRPRLPPRTTGPLIDWEAFTERPFVFITLSMFLNFWGLYFAFFYLGTFARDRIGIEHTQNLVLV
LNGVGVVGRIVPTLIGDRVLGRLNTLIPSSLASSLLIYCWIPVSTQGGLYAFAAVYGVVGGAAQALFP
ASITTMSPDIKKTGTRVGMILSIVSIATLTGPAIEGALIHRAGGSYLYAQIFAATSILVGAFAAIAARIAK
TGWAWNVKA

*FIG. 21*

SEQ ID NO: 5

PROMOTER SEQUENCE OF GAPDH:

CTGCAGAACTACGCCCTCTCACACCCAACTTCCGACTCGACCGGCGGTACGAGCACGACCTACTT
CTACTGCCTGCCATCGACATCCGGGCGGGTCGCTGCCTACCCTGTGCGTTCTGCGCCCTCCCTCGT
CTCGGGAGGCAGTGTCTGACAGAAGCTTTGCGCGCAGTACCCCGTCAAGATGCAACTCTACGCAA
CGTTCGGCACAGAAGTCGCCAAGCTCCGCGCATCGCCGCCTCAAGCTCTCGCGCTGCCCGACGGT
GTCGTCTATTACGAGGCGGAGAAGCTCGAGTTGCCGGCTTTGCCAGCGGCGGTCAAGGTTGAGGT
GGAGACGGAGAAGGCGGGAGTAGCGGGGGAGGACAATGAGGCGAAGGGTGAGATGGTGCTGGT
GGAGACTCTTACGGTGGAGCAGGAGGAGATTGAATTGGGCTCGGGAGTCGTGCAGATTGAGGAG
TCGTTGCTCGTCAAGCTGGAGGTCAGCGGCTGATCCTTCCGTTCGTTGCAAGGATCGTCTGCATGT
TTCGCTTCTCTCAATGACACAACCTGGAGAGCGCTCCCGTCAGCGAGAATCGAGGACATTCCGCA
GCTCGTGAGCAAGCGGAGGTGCGAGGCTCCCTCGAAAGCTGCGCCTCTTCAGACGGCTTGTTCTC
TCCTGCTCTGGTGGGCTGGCCTGACATGTAATGTGCTCCGCCGCAAGTCCGTCGTCGGTCTCAATT
CGACGTTGAAAGGGCATAGCGCAAGGAAGAACCCTCTGCGGACATGCAGAATTACTGGCTCGCC
TGCTCCTTCGTCTACTGGAATAAGTCCTGTCTCGTTAAAGCCCCAACGTCGTTTTTCGACGTTTGT
AAGGCGCAAGAGGTGCTATGGGCTACGCAGGAAGCTGAGAGGACATAGAAGTCGGGGGAGGAA
CGGCGCAGAGCGGCAGTTGCGGAAGCATGAGGAAAGCGAGACGGTCCAGCATCTGCAGCGCCA
ATCCGCAATCTCCTGGTTGAGCCTGCACCGGAAGCGTCGGAACAGTATGCGCAGAGTCGAACGC
AAGTAAGAAAGACGCACCCTCACACTCGCTTACTTCGAGCCATACAACGGATCAAAGCTGCGCG
TATCTCGGCTTGTAAGGGCCGGAAAGCAACCTCGGAGATGGACACGTCACATCACCAACTTATCG
ATCTCGGCCGTCGACGTCGCAGAGAGGGCGAGAGAAGCGGTGAAGGAGGGAAACAACCCCTCG
AGAGCATGATCCGACCGAATCTGCAGCGCAGGAAGCCGTTACAAGCCCGCCTCGAGCGCAGGTC
GGGTCCAGCCGGGGGACGAAACGCGCGAGGCTGATTCGTGAGCGAAGGAAGCCGCATCGACAA
GTTCGCTCCCCTTTGCCCTCTTTCCCATCACCCGTTCTCGCCTTACCCGCTCAGAACAACACCAGA
TCACTCACA

SEQ ID NO: 6

PROMOTER SEQUENCE OF TEF1:

CATGCTGCTGCTGCCCCTCAAAGGTCCTCTCGTCCACGTCCGACGAGTCTGGACAGCTTTCACAGT
CCCGAGAGTGCAAGAGCGAGGCGGGCTCACGGTTCCGCAAAGGAGCGCGAGGTCCGACCGCCGG
CCGGTCTCCTTGCCCGCCTCGCCTCACCTCCTCTTGCAGCAGGTTCACCTCTTCGAGGTCACTCGA
TCGCTCGCAGCGATGCGCAGGTACAAGTACGCTAGGCGAGAGCGTCGAAAGCGGGGTTCTGCGA
GGGACTGGACGCTGCAGAGCGCGGTCGAGAGAGGCTCGAGTGGCGCTTTGACCGCTCGACGCAA
GGCATGCGCTCCTCCGTTTGAGCTCGCAGATACTGCCGTGCGAAGACGAGCATAGGCTGTGGCTG
CGGTAGCAAGGAGCCGGCGAGAGAAAGCTGTGCTCGAGCAGGACGAGAGACGGTCCGCGCGCTT
GAGAAGGTCGAGGTGAGGCGTCGCAACCGGGTTGGATCTCGATTCTCGGCGAACTACGGCTTCG
GCGAGGGCCAAAGCGACGGCAGGCCGCGCAAGCTGGCCAGGCGAGAGCGCGAGAGTCGCGAGC
TGAAGCGGGCGCGGGGTAGAGCAAGCTGGGGAAGCGAGAGAGGGAGAGAGAGAGAGTGAGGG
GGTGGCGAGGTGGAGACGAGGCGAGCGGTTGGCTTGCGCGCGCGAGAGGGATCGAGGCGAG
AGGCGAGCCCCGAGAGTGGAAGGAAGGACGAGGAAACCTGCGTGCGGAGGCGCCGCGCGCGCG
TGCCACCTGGCTGAGCACGGGCCCGAGCTTGAGGGAGCTGGGGGCGCGCGAGCGAGACGAGGGC
AGGGCGAGCCCGCGCGTGGCGGCCGCCTCGCAACCCAAGGCTCGCCCTGGCCGCCGCTCTTGCTC
TCTTTCCTCCACCTTCGCGTCTCACCACTCGAATCTCACTTCATCCATC

FIG. 22

SEQ ID NO: 7

Promoter sequence of P9 that controls MCRCa-Split

*GTTCTGTAGGAGAGGGTTGGTAGGTTGTGAGGGTGGTGTGAGGGTGCGGGTAACCGGGA*
*AGTGTTCGGACGGGTGGGAAGGAAGGAGAGGGACGACGAGCCTGCGCGACGAGGTTGA*
*TCGACCGCGCGCGCGCCAAACAATCAATACCTAGGCTCGTGCGTCTGTTACTAGGTCAAC*
*AGTAAGCCTAGTTATGCGTACATCCGCATCAATTCTCGTACGCACCTTCTAGAGCTGGGCA*
*AACAAAGCCACTTCCCGCGCGCCTCATAGCTCGTCCTTCGCCACGCTCCTCTCTCTCCCTT*
*CTTCCCACCACCTTCAGCACACCGGCCTCGCCGTCTCGACACGCTCCTCTCCTCACCTCA*
*ACCCCAACAACACCTCAATCAAACAGTGCGTCCCGTCCAGCTCAAACAGCGACCGAGCC*
*GAGCTGACCTTGTCCCGCACTTCCCGCAACAG*

FIG. 23

MODIFIED YEAST MICROORGANISMS TO INCREASE YIELD OF 3-HYDROPROPIONIC ACID

STATEMENT OF GOVERNMENT INTEREST

This invention was made with Government support under Contract No. DE-NA0003525 awarded by the United States Department of Energy/National Nuclear Security Administration. The U.S. Government has certain rights in the invention.

REFERENCE TO A SEQUENCE LISTING APPENDIX

A sequence listing appendix including XML file in accordance with WIPO ST.26 accompanies this application. The appendix includes a file named "SD-16353.xml," created on Feb. 28, 2022 (size of 16.5 kilobytes), which is hereby incorporated by reference in its entirety.

FIELD

The present disclosure relates to methods and engineered microbial hosts useful for treating biomass hydrolysates. In particular, the disclosure relates to a modified oleaginous *Rhodosporidium* yeast for improving production of 3-hydropropionic acid from a lignocellulosic hydrolysate, e.g., from a biomass source.

BACKGROUND

3-Hydropropionic acid ("3HP") has been identified as a top value-added platform molecule, as its derivatives are used industrially in many multi-billion dollar markets globally. 3HP is a precursor to a number of high-value commodity chemicals such as acrylic acid, 1,3-propanediol, methacrylic acid, propylene glycol. These chemicals are appealing industrial targets for bioplastics, metal lubricants, and coatings, which all represent large markets. For example, 4.5 million metric tons of acrylic acid is made industrially from hydrocarbon-based propylene, accounting for a $7-10 billion market alone. However, polypropylene is a heavily carbon-intensive feedstock, and more environmentally friendly alternatives are desirable.

There is a need to valorize or convert lignocellulosic biomass into valuable products. In particular, biomass sources from corn production, such as corn stover or distillers' dried grains (DDGs), make up a large segment of unused biomass in the United States. Production of DDGS has dramatically increased in the last few decades. Despite potential utility for this product for animal feed blending, market adoption of the feedstock has been limited. Such co-products, as well as other biomass products, can contain high value components that are difficult to recover and isolate. Accordingly, there is a need for methods and tools to facilitate such production in an effective and efficient manner.

Accordingly, microbial production of 3HP would be desirable as it is sustainable and environmentally friendly, uses cheap feedstocks as substrates, if its potential for high yields from a variety of metabolic pathways can be realized.

SUMMARY

The present disclosure relates to methods and engineered hosts to convert a renewable material and energy source into 3HP. In particular, an exemplary engineered Rhodosporidum, e.g., *Rhodosporidium toruloides* host is described that produces/expresses one or more enzymes that can convert pretreated, lignocellulosic biomass or other sugar-containing raw material energy sources into 3HP. Methods of using such hosts on are also described herein.

To lower this cost barrier, the malonyl-CoA pathway has been engineered to produce 3HP in *R. toruloides* at titers comparable to the highest ever achieved in conventional hosts such as *S. cerevisiae*. Utilizing *R. toruloides* to convert complex biomass sources into 3HP and its derivatives at a lower cost can benefit both the ecology of the planet and the provide a revenue source for those engaged in converting the biomass.

*R. toruloides* naturally has a high metabolic flux towards malonyl-CoA. This pathway was exploited to produce 3HP. Upon finding the yeast capable of catabolizing 3HP, functional genomics and metabolomic analysis were employed to identify the catabolic pathways.

Through the course of research described herein, two main bottlenecks in 3HP production from *R. toruloides* were identified and solved: 3HP degradation and transport. Deletion of a putative malonate semialdehyde dehydrogenase gene encoding an oxidative 3HP pathway was found to significantly reduce 3HP degradation. RB-TnSeq was used to identify genes involved in 3HP catabolism and two potential active catabolic routes were identified. Monocarboxylate transporters to promote 3HP transport were explored through RNA-seq and proteomics, and a 3HP transporter was identified by RNA-seq and proteomics. Combining these strain engineering efforts with media optimization, the 3HP titer reached 45.4 g/L in a 2-L fedbatch bioreactor. This represents one of the highest 3HP titers reported in eukaryotes, and is believed to be the highest titer produced from lignocellulosic hydrolysate. This work demonstrates microbial production of 3HP in *R. toruloides* from lignocellulosic hydrolysate at high titers, and it represents a significant step toward enabling industrial production of 3HP in the future.

Definitions

As used herein, the term "about" means+/−10% of any recited value. As used herein, this term modifies any recited value, range of values, or endpoints of one or more ranges.

In any of the embodiments herein, a contiguous fragment can include at least 5, 10, 11, 12, 13, 14, 15, 16, 17, 18, 19, 20, 21, 22, 23, 24, or 25 contiguous nucleotides from a full-length nucleic acid sequence. In some embodiments, the contiguous fragment includes from about 5 to about 100 nucleotides (e.g., from 5 to 10, 5 to 25, 5 to 50, 5 to 75, 5 to 100, 10 to 25, 10 to 50, 10 to 75, 10 to 100, 20 to 25, 20 to 50, 20 to 75, 20 to 100, 25 to 50, 25 to 75, 25 to 100, 50 to 75, 50 to 100, or 75 to 100 nucleotides).

In any of the embodiments herein, a contiguous fragment can include at least 5, 6, 7, 8, 9, 10, 11, 12, 13, 14, 15, 16, 17, 18, 19, 20, 25, 50, 75, 90, 100, 150, 200, 250, 300, or 350 contiguous amino acids from a full-length amino acid sequence. In some embodiments, the contiguous fragment includes from about 5 to about 350 amino acids (e.g., from 5 to 10, 5 to 25, 5 to 50, 5 to 75, 5 to 100, 5 to 150, 5 to 200, 5 to 250, 5 to 300, 10 to 25, 10 to 50, 10 to 75, 10 to 100, 10 to 150, 10 to 200, 10 to 250, 10 to 300, 10 to 350, 20 to 25, 20 to 50, 20 to 75, 20 to 100, 20 to 150, 20 to 200, 20 to 250, 20 to 300, 20 to 350, 25 to 50, 25 to 75, 25 to 100, 25 to 150, 25 to 200, 25 to 250, 25 to 300, 25 to 350, 50 to 75, 50 to 100, 50 to 150, 50 to 200, 50 to 250, 50 to 300, 50 to 350, 75 to 100, 75 to 150, 75 to 200, 75 to 250, 75 to 300, and 75 to 350 amino acids).

In any embodiment herein, at least 70% sequence identity to a reference sequence can include at least 73%, 80%, 90%, 95%, 96%, 97%, 98%, or 99% sequence identity to the full reference sequence (e.g., the reference nucleic acid sequence or the reference amino acid sequence). Sequence identity calculation is based on the number of amino acids that differ from the total number of amino acids on a protein level. An example of a software package for calculating sequence identity is BLAST, which is applicable to the present invention by entering a string corresponding to the sequences herein.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs. For any nucleic acid sequence described herein, uracil (U) may be thymine (T), and T may be U.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

A nucleoside modification may include, but is not limited to, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, $N^4$-acetylcytidine, 5-formylcytidine, $N^4$-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2, 6-diaminopurine, 1-methyladenosine, $N^6$-methyladenosine, $N^6$-isopentenyladenosine, $N^6$-(cis-hydroxy-isopentenyl) adenosine, 2-methylthio-$N^6$-(cis-hydroxyisopentenyl) adenosine, $N^6$-glycinylcarbamoyladenosine, $N^6$-threonyl-carbamoyladenosine, 2-methylthio-$N^6$-threonyl carbamoyladenosine, $N^6,N^6$ dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, $N^2$-methyl-guanosine, $N^2,N^2$-dimethylguanosine, 8-oxo-guanosine, 7-methyl-8-oxo-guanosine, 1-methyl-6-thio-guanosine, $N^2$-methyl-6-thio-guanosine, and $N^2,N^2$-dimethyl-6-thio-guanosine, and combinations thereof.

A sugar modification may include, but is not limited to, a locked nucleic acid (LNA), in which the 2'-hydroxyl is connected by a $C_{1-6}$ alkylene (e.g., a multivalent (e.g., bivalent, trivalent, tetravalent, etc.) form of an alkyl group) or $C_{1-6}$ heteroalkylene (e.g., a divalent form of an alkylene group containing one, two, three, or four non carbon heteroatoms) or (e.g., independently selected from the group consisting of nitrogen, oxygen, phosphorous, sulfur, or halo) bridge to the 4'-carbon of the same ribose sugar, replacement of the oxygen in ribose (e.g., with S, Se, or alkylene, such as methylene or ethylene), addition of a double bond (e.g., to replace ribose with cyclopentenyl or cyclohexenyl), ring contraction of ribose (e.g., to form a 4-membered ring of cyclobutane or oxetane), ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone), multicyclic forms (e.g., tricyclic), and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with a-L-threo-furanosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar.

A backbone modification may include, but is not limited to, 2'-deoxy- or 2'-O-methyl modifications. Exemplary modifications include modifications to the 2' position of a nucleic acid, such as 2'-O-methyl, 2'-halo (e.g., 2'-fluoro, 2'-chloro, 2'-bromo, or 2-iodo), 2'-alkyl (e.g., 2'-methyl, 2'-ethyl, 2'-propyl, 2'-allyl, etc., in which alkyl can be an optionally substituted alkyl, as defined herein), 2'-aryl (e.g., 2'-phenyl, in which aryl can be an optionally substituted aryl, as defined herein), 2'-alkaryl (e.g., 2'-benzyl, in which alkaryl can be an aryl group, as defined herein, attached to the parent molecular group through an alkylene group, in which an alkylene group can be a multivalent (e.g., bivalent, trivalent, tetravalent, etc.) form of an alkyl group, as described herein), 2'-amino (e.g., 2'—$NH_2$, etc., in which amino can be $NR^{N1}R^{N2}$, where each of $R^{N1}$ and $R^{N2}$ is, independently, H, alkyl, or alkaryl, or $R^{N1}$ and $R^{N2}$, taken together with the nitrogen atom to which each are attached, form a heterocyclyl group), 2'-alkoxy (e.g. 2'-O-methoxy, 2'-O-ethoxy, etc., in which alkoxy can be —OR, where R is an optionally substituted alkyl group, as described herein), 2'-alkylamino (e.g., 2'-O-methylamino, 2'-O-ethylamino, etc.), 2'-O-alkylamino (e.g., 2'-O-methylamino, 2'-O-ethylamino, etc., in which alkylamino can be an alkyl group, as defined herein, substituted by an amino group, as defined herein), 2'-azido (in which azido is an —$N_3$ group), 2'-O-cyanoalkyl (e.g., 2'-O-cyanomethyl, etc., in which cyanoalkyl can be an alkyl group, as defined herein, substituted by a cyano group (a —CN group)), 2'-O-alkoxyalkyl (e.g., 2'-O-(2-methoxyethyl), etc., in which alkoxyalkyl can be an alkyl group, as defined herein, which is substituted with an alkoxy group, as defined herein), etc.

A phosphate group modification may include, but is not limited to, phosphorothioate, phosphoroselenates, boranophosphates, boranophosphate esters, hydrogen phosphonates, phosphoramidates, phosphorodiamidates, alkyl or aryl phosphonates, phosphotriesters, phosphorodithioates, bridged phosphoramidates, bridged phosphorothioates, or bridged methylene-phosphonates.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 73%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2 (4): 482-9.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1150, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (G), alanine (A), valine (V), leucine (L), and isoleucine (I); a group of amino acids having aliphatic-hydroxyl side chains consists of serine(S) and threonine (T); a group of amino acids having amide containing side chains consisting of asparagine (N) and glutamine (Q); a group of amino acids having aromatic side chains consists of phenylalanine (F), tyrosine (Y), and tryptophan (W); a group of amino acids having basic side chains consists of lysine (K), arginine (R), and histidine (H); a group of amino acids having acidic side chains consists of glutamic acid (E) and aspartic acid (D); and a group of amino acids having sulfur containing side chains consisting of cysteine (C) and methionine (M). Exemplary conservative amino acid substitution groups are valine-leucine-isoleucine (VLI), phenylalanine-tyrosine (FY), lysine-arginine (KR), alanine-valine (AV), glycine-serine (GS), glutamate-aspartate (ED), and asparagine-glutamine (NQ), as well as any described herein. Accordingly, for any polypeptide sequence described herein, the present invention may also encompass one or more conservative amino acid substitutions.

For a polypeptide sequence described herein, the recited sequence may also encompass a conservative subset, which can include a conservation between groups of strongly similar properties or a conservation between groups of weakly similar properties, as described herein. Exemplary conservative subsets include those having a conservation between groups of strongly similar properties; as well as those having a conservation between groups of weakly similar properties, as known to those of ordinary skill in the art.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2 (4): 482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, CLUSTAL OMEGA, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence can have at least about 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length amino acid sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, WI, 53705). Such software may match similar sequences by assigning degrees of homology to various substitutions, deletions, and other modifications. If any conflicting results are obtained for anything recited in the claims appended hereto, the Sequence Analysis Software Package of the Genetics Computer Group, University of Wisconsin Biotechnology Center, 1710 University Avenue, Madison, WI, 53705 should be used.

A "host," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

As used herein, the term "exogenous" in reference to a nucleic acid or a polypeptide refers to a nucleic acid or a polypeptide that is not normally or naturally found in and/or produced by a given bacterium, organism, or cell in nature. As used herein, the term "endogenous" in reference to a nucleic acid or a polypeptide refers to a nucleic acid or a polypeptide that is normally found in and/or produced by a given bacterium, organism, or cell in nature.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence. Exemplary promoter sequences can include a nucleic acid regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation, as well as protein binding domains (consensus sequences) responsible for the binding of RNA polymerase. Eukaryotic promoters will often, but not always, contain "TATA" boxes and "CAT" boxes. Prokaryotic promoters can contain Shine-Dalgarno sequences in addition to the −10 and −35 consensus sequences.

An "expression control sequence" can be a nucleic acid sequence that controls and regulates the transcription and translation of another nucleic acid sequence. A coding sequence is "under the control" of transcriptional and translational control sequences in a cell when RNA polymerase transcribes the coding sequence into mRNA, which is then translated into the protein encoded by the coding sequence. Exemplary transcriptional and translational control sequences are DNA regulatory sequences, such as promoters, enhancers, polyadenylation signals, terminators, and the like, that provide for the expression of a coding sequence in a host cell.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

In accordance with the present disclosure, there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the disclosed technology will be apparent from the following description and the claims.

BRIEF DESCRIPTION OF THE DRAWINGS

In FIG. 18A, cell growth, residual concentration of glucose and xylose, and consumed glucose concentrations are shown. In FIG. 18B, 3HP titers and yields are shown.

FIG. 20 discloses SEQ ID NOS: 1 and 2.
FIG. 21 discloses SEQ ID NOS: 3 and 4.
FIG. 22 discloses SEQ ID NOS: 5 and 6.
FIG. 23 discloses SEQ ID NO: 7.

DETAILED DESCRIPTION

Figure 1:
FIG. 1 shows two possible reaction pathways, a reductive and oxidative pathway for degrading 3HP.
Figure 1:

The present disclosure relates, in part, to methods and compositions (e.g., engineered hosts) for use in converting biomass to 3HP. It was determined $MCR_{ca-split}$ was the gene in *R. toruloides* that encoded the pathway that produces 3HP. In particular embodiments, the methods include use of an engineered *Rhodosporidium* yeast, such as *R. toruloides*, the engineered *R. toruloides* having the RT04_8975 (SEQ ID NO: 1) gene deleted from its genome combined with a lignocellulosic hydrolysate, sourced, for example, from a biomass. An engineered transporter is utilized to improve 3HP titers. An engineered promoter that improves 3HP titers is also incorporated into the reaction mixture (or fermentation broth) by addition to the *R. toruloides* genome, for example, by modified lithium acetate transformation.

While multiple chemical synthesis routes have been proposed to produce 3HP, their feasibility for large-scale production has been limited due to low yield, high cost of starting material, toxic or non-recyclable catalysts, and environmental incompatibility. There are at least three main biological pathways for producing 3HP via the metabolites glycerol, β-alanine, and malonyl-CoA. The glycerol reduction pathway is used natively by organisms such as *Klebsiella pneumonia* to produce 3HP. See Jiang, J., et al., 2018. Efficient 3-hydroxypropionic acid production from glycerol by metabolically engineered *Klebsiella pneumoniae*. Bioresour Bioprocess 5, 34. and Li, Y., et al., 2016. High Production of 3-Hydroxypropionic Acid in *Klebsiella pneumoniae* by Systematic Optimization of Glycerol Metabolism. Sci Rep 6, 26932, incorporated herein by reference. Modification of this native pathway has resulted in one of the highest reported 3HP titers of 84 g/L from glycerol as a feedstock. Most of the studies on the glycerol pathway have used bacterial hosts and porting the glycerol route to eukaryotic hosts such as *Saccharomyces cerevisiae* is challenging due to the lack of cofactor vitamin B12. See Borodina, I., et al., 2015. Establishing a synthetic pathway for high-level production of 3-hydroxypropionic acid in *Saccharomyces cerevisiae* via β-alanine. Metab. Eng 27, 57-64 incorporated herein by reference. As a result, most studies engineering heterologous production of 3HP in eukaryotic hosts have focused on the β-alanine and malonyl-CoA pathways. See Ji, R.-Y., et al., 2018. Metabolic Engineering of Yeast for the Production of 3-Hydroxypropionic Acid. Front Microbiol 9.

A promising biosynthetic route for 3HP production is through the malonyl-CoA pathway. This pathway has been successfully expressed heterologously and described in publications by various authors to produce 3HP in *S. cerevisiae, Escherichia coli, Methylobacterium extorquens, Synechocystis*, and *Schizosaccharomyces pombe*. An enzyme used in these studies is the malonyl-CoA reductase (MCR) originally involved in the carbon fixation pathway of the photosynthetic bacteria *Chloroflexus aurantiacus*, an organism capable of using $CO_2$ as its sole carbon source. Hügler, M., et al., 2002. Malonyl-Coenzyme A Reductase from *Chloroflexus aurantiacus*, a Key Enzyme of the 3-Hydroxypropionate Cycle for Autotrophic $CO_2$ Fixation. J Bacteriol 184, 2404-2410, incorporated herein by reference. In *C. aurantiacus*, for example, MCR performs a two-step reduction of malonyl-CoA to 3HP. The bifunctional enzyme contains an alcohol dehydrogenase N-terminus and aldehyde dehydrogenase C-terminus that perform the $2^{nd}$ and $1^{st}$ steps, respectively. The reactions performed by the bifunctional enzyme, malonyl-CoA reductase from *C. aurantiacus* ($MCR_{Ca}$), are split into the N- and C-terminal components. The C-terminus has been demonstrated to be the rate-limiting step when expressed in *E. coli*, and 3HP titers were increased 270-fold when each domain was expressed independently. See Liu, C., et al., 2016. Functional balance between enzymes in malonyl-CoA pathway for 3-hydroxypropionate biosynthesis. Metab Eng 34, 104-111. Liu, C., et al., 2013. Dissection of Malonyl-Coenzyme A Reductase of *Chloroflexus aurantiacus* Results in Enzyme Activity Improvement. PLOS One 8, e75554.

In an embodiment, to further optimize the process and materials for increasing yield of the 3HP product, additional steps can be taken. For example, the gene encoding malonyl-CoA reductase from *C. aurantiacus* ($MCR_{Ca}$) split into its N- and C-terminus can be codon optimized for the engineered host. The sequence for codon-optimized $MCR_{Ca}$ is disclosed in FIG. 20 as SEQ ID NO: 2 (N-terminus) and FIG. 21 as SEQ ID NO: 3 (C-terminus). Codon optimization was performed using a *R. toruloides*-specific codon usage table that tallied the frequency of codon usage for all protein-encoding sequences in the genome. Using this table, $MCR_{Ca}$ was codon optimized by choosing the most frequently used codons.

The oleaginous basidiomycete *Rhodosporidium toruloides* is an attractive host for industrial scale production of many bioproducts. Not only does it readily co-consume the complex C5 and C6 sugar mixtures commonly derived from lignocellulosic biomass and is tolerant to many inhibitors in the biomass hydrolysate, it can also grow to very high cell densities. *R. toruloides* has been engineered to produce high titers of various bioproducts from lignocellulosic feedstocks, including fatty alcohols (Fillet, S., Adrio, J. L., 2016, Microbial production of fatty alcohols. World J Microbiol Biotechnol 32, 152; Liu, D., 2020, Exploiting nonionic surfactants to enhance fatty alcohol production in *Rhodosporidium toruloides*. Biotechnol Bioeng 117, 1418-1425; Schultz, J. C., et al., 2022. Metabolic engineering of *Rhodotorula toruloides* IFO0880 improves C16 and C18 fatty alcohol production from synthetic media. Microb Cell Fact 21, 26) indigoidine (Wehrs et al., 2019, Sustainable bioproduction of the blue pigment indigoidine: Expanding the range of heterologous products in *R. toruloides* to include non-ribosomal peptides. Green Chemistry 21, 3394-3406, and terpenes Das, L., et al., 2021, Seawater-based one-pot ionic liquid pretreatment of sorghum for jet fuel production. Bioresour Technol Rep 13, 10062; Geiselman, G. M., et al . . . , 2020a, Conversion of poplar biomass into high-energy density tricyclic sesquiterpene jet fuel blendstocks. Microb Cell Fact 19, 208). *R. toruloides* has been found to exhibit a naturally high flux of acetyl-CoA into malonyl-CoA due to high expression of acetyl-CoA carboxylase (ACC) Liu, H., 2009, Comparative proteomic analysis of *Rhodosporidium toruloides* during lipid accumulation. Yeast 26, 553-566, thus making it a promising host for 3HP production via the malonyl-CoA pathway. Furthermore, the genetic engineering toolbox for manipulating this once-niche organism is becoming increasingly robust with the establishment of strong promoters (Nora, L. C., 2019, A toolset of constitutive promoters for metabolic engineering of *Rhodosporidium toruloides*. Microb Cell Fact 18, 117, incorporated herein by reference). A toolset of constitutive promoters for metabolic engineering of *Rhodosporidium toruloides*. Microb Cell Fact 18, 117, incorporated herein by reference) and advanced CRISPR-based DNA editing strategies (Jiao, X., et al., 2019. Developing a CRISPR/Cas9 System for Genome Editing in the Basidiomycetous Yeast *Rhodosporidium toruloides*. Biotechnol J 14, 1900036; Otoupal, et al., 2019. Multiplexed CRISPR-Cas9-Based Genome Editing of *Rhodosporidium toruloides*. mSphere 4; Schultz, J. C., et al., 2019, Development of a CRISPR/Cas9 system for high efficiency multiplexed gene deletion in *Rhodosporidium toruloides*. Biotechnol Bioeng 116, 2103-2109, all of which are incorporated herein by reference).

The production of 3HP in *R. toruloides* is disclosed herein. The malonyl-CoA to 3HP pathway was constructed through expression of MCR from *C. aurantiacus* ($MCR_{ca}$). While expressing the full-length $MCR_{ca}$ gene in *R. toruloides* failed to produce 3HP, expressing the N- and C-termini independently led to successful 3HP production with titers of 2.2 g/L. However, the inventors observed significant consumption of 3HP subsequent to production. To improve 3HP production, an RB-TDNA seq experiment was performed to identify and delete genes involved in 3HP catabolismesearch was also conducted to identify potential transporters that export 3HP under the hypothesis that enhanced export would drive the reaction kinetics toward 3HP. Coupled with media optimization, these strategies led to the production of 19.2 g/L 3HP during fermentation of hydrolysate produced from lignocellulosic feedstock, representing an 8.7-fold increase from the parent strain at the bench scale. Optimization of media and culture conditions further enhanced productivity, leading to 45.4 g/L titers of 3HP in a fed-batch bioreactor from cornstover hydrolysate with minimal nutrient addition. This research demonstrated one of the highest 3HP titers from the malonyl-CoA pathway, and the highest titer produced from lignocellulosic hydrolysate. This highlights the value of *R. toruloides* and enables it as a promising industrial host for the production of 3HP, and potentially other biofuels and bioproducts.

As mentioned above, while effective in *C. aurantiacus*, expressing the full-length $MCR_{ca}$ gene in *R. toruloides* failed to produce 3HP. However, after significant experimentation on different pathways for production of 3HP in *R. toruloides*, it was determined that expressing the N- and C-termini independently led to successful 3HP production.

It was discovered early in this work that *R. toruloides* has the capacity to consume 3HP in the absence of glucose. Previous studies have proposed two potential routes for 3HP degradation, including a reductive pathway and an oxidative pathway. See Yang. Y.-M., et al., 2017. Production of 3-hydroxypropionic acid in engineered *Methylobacterium extorquens* AMI and its reassimilation through a reductive route. Microb Cell Fact 16, 179, incorporated herein by reference. The reductive pathway converts 3HP to propionyl-CoA, which then enters the TCA cycle through the 2-methylcitrate cycle (FIG. 1).

The oxidative pathway involves a one-step conversion of 3HP into malonate semialdehyde (3OP), which will be then converted to acetyl-CoA through 3OP dehydrogenase. To elucidate which pathway *R. toruloides* employs to consume 3HP, an RB-TDNA Seq experiment was performed. The RB-TDNAseq method is described in more detail by Coradetti, S. T., et al., "Functional genomics of lipid metabolism in the oleaginous yeast *Rhodosporidium toruloides*," eLife 7 (2018), incorporated herein by reference.

The results suggested correlation between the 3HP degradation with the branched chain amino acid (valine and leucine) pathway in *R. toruloides*, which corresponds to the reductive degradation pathway that produces propionyl-CoA (FIG. 1). Indeed, a number of genes involved in the valine pathway were ranked among the top 30 genes that showed most significant fitness defects in 3HP. See FIG. 2, which shows fitness scores of potential genes involved in 3HP catabolism Fitness scores were obtained in several carbon sources, including 3HP and a number of reference carbon sources. The top 100 genes that exhibit most significant fitness defects in 3HP were selected, out of which genes directly associated with metabolic enzymatic reactions were ranked based on their fitness defects in 3HP and plotted.

A biosensor designed based upon a 3HP-responsive transcription factor was found to also be induced in the presence of valine, highlighting the possible connection between valine and 3HP consumption. See Nguyen, N.H., et al., 2019, Development of Biosensor for 3-Hydroxypropionic Acid. Biotechnology and Bioprocess Engineering 24, 109-118. Furthermore, increased heptadecanoic acid levels were observed through a metabolomic analysis, which could be caused by a higher level of 3HP-derived propionyl-CoA.

It was found that the oxidative degradation pathway could be curtailed by deleting ALD6, (the RTO4_8975 encoded protein) and this eliminated a large portion of 3HP catabolism. This indicated this pathway accounts for the majority of the 3HP catabolic activity in this host. Without being bound to theory, to further reduce 3HP catabolism, disrupting the 3HP reductive degradation pathway may be helpful; however, caution should be taken as the pathway likely overlaps with the native branched-chain amino acid pathway.

As disclosed herein, it was determined that the putative gene responsible for 3HP consumption was RTO4_8975, and the inventors identified and successfully deleted RTO4_8975 from the *R. toruloides* genome.

Engineered microbial hosts disclosed herein can be derived from a Eukaryote microorganism, including yeast, such as a Basidiomycete yeast. The terms "cell," "microbial cells," and "microbes" are used interchangeably with the term microorganism. The term "host" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

In an embodiment, the microbial host is a *Rhodosporidium* microorganism. It has been reported that these yeast cells are globose, ovoid, or elongate, and that budding is multilateral or polar. Ballistoconidia do not form. Carotenoid pigments are visible and the cultures are pink to orange in color. Some species are heterothallic, and others are self-fertile. See José Paulo Sampaio, in "The Yeasts" (Fifth Edition), 2011 (publisher summary).

The genus *Rhodosporidium* includes, for example, *R. toruloides, R. azoricum, R. fluviale, R. lusitaniae, R. babjevae, R.* diobovanon, *R. paludigenum. R. sphaerocarpum*, and *R. kratochvilovae*. Such hosts can be transformed to provide an engineered host. *R. toruloides*, in particular, is an attractive host, as it is compatible with many hydrolysates (i.e., tolerant to various biomass hydrolysate inhibitors), has naturally high concentration of AcCoA used to form lipid droplets (i.e., TAGs) as a form of energy storage that can be exploited for fatty acid-like products and terpenes.

In an embodiment, the engineered host can be derived from a Basidiomycete organism so long as the Basidiomycete in its natural form has a gene with 70% or greater sequence identity to RT04_8975 in its genome, such as, for example, 73% or greater, 80% or greater, 90% or greater, or 98% or greater sequence identity to RT04_8975 in its genome. Being "derived from" in this context means that the organism is subjected to the gene deletion described herein. The engineered host has the gene with 80% or greater, 90% or greater, 95% or greater, or 98% or greater sequence identity to the RT04_8975 gene deleted from its genome. The base Basidiomycete organism from which the engineered organism is derived can be selected from Rhodosporodium and any members thereof that in its natural form contains the gene with 70% or greater sequence identity to RT04_8975 gene, such as, for example, 73% or greater, 80% or greater, 90% or greater, or 98% or greater sequence identity to RT04_8975 in its genome.

Exemplary methods of engineering of the base organism include, for example, gene deletion or heterologous gene integration via lithium acetate or CRISPR-Cas9-mediated transformations (Otoupal, P. B., et al., "Multiplexed CRISPR-Cas9-Based Genome Editing of *Rhodosporidium toruloides*," MSphere 4 (2019) incorporated herein by reference), or AtMT (Zhuang, X., et al. "Monoterpene production by the carotenogenic yeast *Rhodosporidium toruloides*," Microb. Cell Fact. 18, 54 (2019) incorporated herein by reference.)

Exemplary sources of glucose and other materials for the engineered yeast to act upon to generate 3HP include a glucose and xylose containing material, such as is found in various biomass or biomass-derived materials. Glucose and xylose are present in biomass hydrolysate, and are derived from cellulose and hemicellulose Lignin may also be present in the biomass material and may, e.g., be formed from a combination of one or more monomers, such as a monolignol monomer, a p-coumaryl alcohol or an alkoxyl form thereof (e.g., a methoxylated form, including mono- and di-methoxylated forms), a coniferyl alcohol or an alkoxyl form thereof (e.g., a methoxylated form), a coumaryl alcohol of an alkoxyl form thereof (e.g., a methoxylated form), and a sinapyl alcohol or an alkoxyl form thereof (e.g., a methoxylated form). In other embodiments, lignin or a lignin derivative can be characterized by the presence of one or more aromatic functional groups, such as a p-hydroxyphenyl group, a guaiacyl group, and/or a syringyl group.

Lignin can have different compositions depending on the plant material from which the lignin is derived. Exemplary lignin can include softwood lignin (e.g., derived from softwood and including of from about 25% to about 30% (w/w) of lignin), compression wood lignin (e.g., derived from compression wood and including of from about 35% to about 40% (w/w) of lignin), typical hardwood lignin (e.g., derived from hardwood and including of from about 20% to about 25% (w/w) of lignin), tropical hardwood lignin (e.g., derived from tropical hardwood and including of from about 30% to about 40% (w/w) of lignin), tension wood lignin (e.g., derived from tension wood and including of from about 20% to about 25% (w/w) of lignin), wheat lignin (e.g., derived from wheat, including any useful part of plant, such as the root, leaves, shoots, and/or stems), maize lignin (e.g., derived from maize, including any useful part of plant, such as the root, leaves, shoots, and/or stems; and including of from about 20% to 75% (w/w) of lignin), mixed grasses lignin (e.g., derived from mixed grasses, including any useful part of plant, such as the root, leaves, shoots, and/or stems).

The energy and material source can include various monosaccharides other than glucose, such as, e.g., pectin-derived monosaccharides, dextrose, fructose, galactose, glucose, or maltose, oligosaccharides, polysaccharides (e.g., cellulose, hemicellulose, or starch), cellulosic material, fatty acids (e.g., saturated or unsaturated fatty acids), biomass hydrolysates, metabolic intermediates (e.g., acetate, lactate, or succinate), alcohols and sugar alcohols (e.g., ethanol, ethylene glycol, glycerol, inositol, malitol, mannitol, sorbitol, or xylitol), lignin and lignin compounds (as discussed above), plants and plant products (e.g., corn, liquefied corn meal, corn steep liquor (a byproduct of corn wet milling process that contains nutrients leached out of corn during soaking), corn stover, corn fiber, rice straw, woody plants, herbaceous plants, molasses, etc., which can be found in, for example, in the stems, leaves, hulls, husks, and cobs of plants; or in the leaves, branches, and wood of trees), herbaceous material, agricultural residues, forestry residues, municipal solid wastes, waste paper, as well as pulp and paper mill residues, or mixtures thereof.

After preventing 3HP consumption by deleting catabolic genes, the focus was shifted to improving production of 3HP by enhancing its export outside of the cell. Metabolomic analysis of MCR$_{Ca\text{-}Split}$ indicated that there was intracellular accumulation of 3HP.

Figure 3:
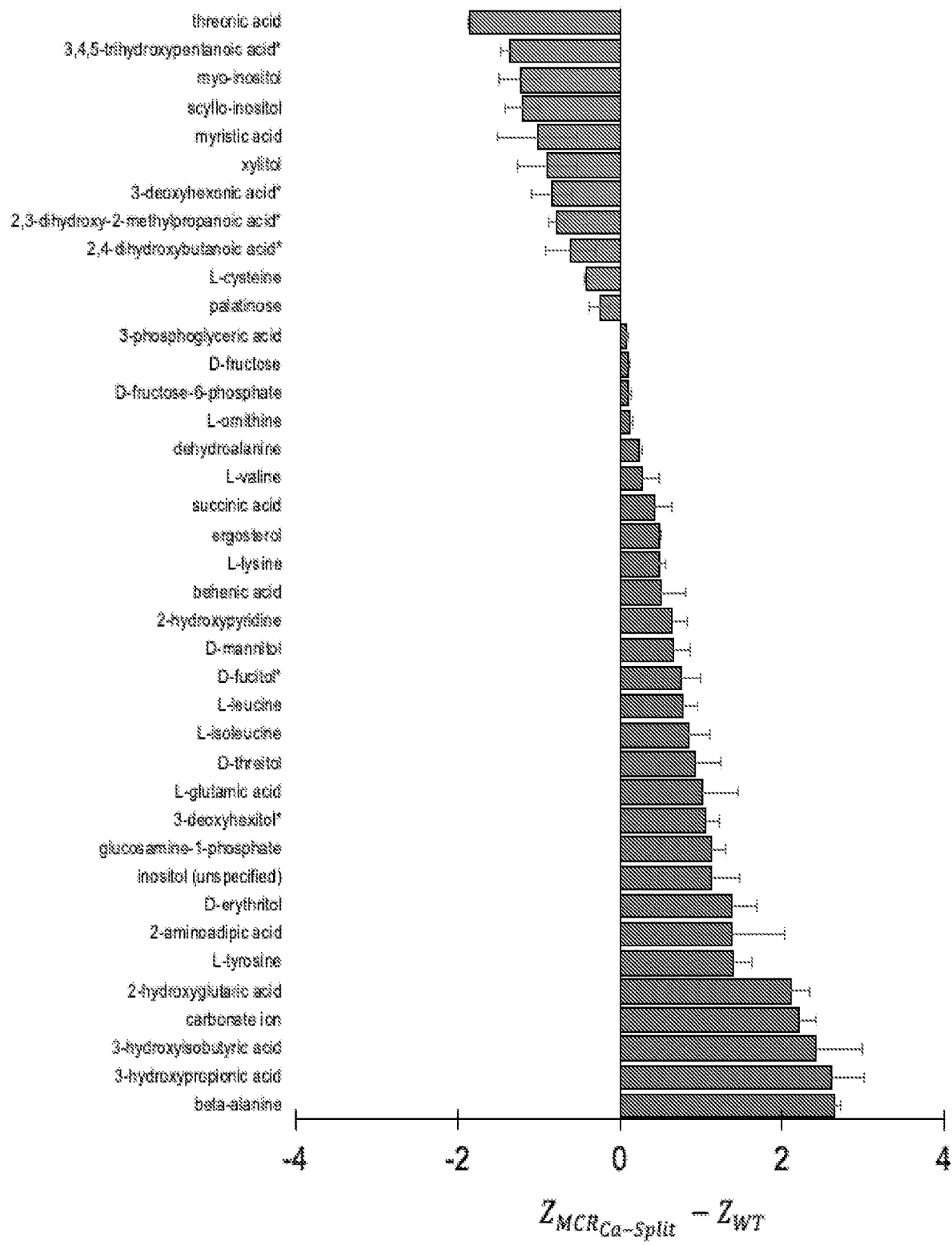
FIG. 3 is a plot of differences in Z-scores of a metabolomic analysis that represents differentially accumulated metabolites in $MCR_{Ca-Split}$. $MCR_{Ca-Split}$ and WT *R. toruloides* that were cultured in Ambr® 250 and the cell pellets were collected for metabolomic analysis after 4 days.

FIG. 3 shows this metabolomic analysis that represents differentially accumulated metabolites in MCR$_{Ca\text{-}Split}$. MCR$_{Ca\text{-}Split}$ and WT R. toruloides that were cultured in Ambr® 250 and the cell pellets that were collected for metabolomic analysis after 4 days. The difference in Z-score was plotted and shown in FIG. 3.

This suggested that engineering enhanced 3HP transport to facilitate the export of 3HP from the cell would improve 3HP titers. It is believed that there are no 3HP transporters in eukaryotes reported in the literature, although a few transporters have been characterized and reported in the literature for monocarboxylic acids with similar chemical structures to 3HP, such as lactic acid and propionic acid. This was a starting point for determining viable transporters. Accordingly, two R. toruloides monocarboxylic acid transporters were tested that were homologous to two characterized lactic acid transporters in S. cerevisiae, Ady2 (RTO4_10658) and JEN1 (RTO4_10184) under the control of a pTEF1 and pPKG1 promoter, respectively. As further detailed below, in addition to targeting transporters based on molecular overlap, a candidate 3HP transporter from Aspergillus pseudoterreus was identified and expressed.

In an embodiment, the biomass hydrolysate is nitrogen deficient and is supplemented with a nitrogen source. Two sources, for example, urea and ammonium sulfate, are used in culturing the R. toruloides. Therefore, when producing an acidic product (e.g., 3HP), addition of urea to the biomass hydrolysate provides the nitrogen while also acting as a buffer to the acidic product. This may increase yields because the fermentation approaches complete sugar utilization within growth-permitting pH range. Improvements may also come from shifts in nitrogen metabolism and shifts in expression of genes directly related to the 3HP pathway. These latter effects can be seen in FIG. 15. Similar results can likely be achieved by addition of another base coupled with a pH-neutral nitrogen source such as yeast extract. Such nitrogen sources coupled with buffers or other pH control mechanism should reach relatively high titers.

It has been recognized that process optimization of cultivation conditions is valuable to improve bioproduct titers, rates and yields. Previous studies in R. toruloides have found that the nitrogen source and C:N ratios have significant impacts on various bioproducts. As part of this research, it was found that the use of urea as the nitrogen source significantly enhanced 3HP production compared to ammonium sulfate, which is consistent with a previous study that engineered R. toruloides to produce indigoidine. (Wehrs, et al., supra). These findings are also in agreement with a previous study Evans, C. T., Ratledge, C., 1984, Influence of Nitrogen Metabolism on Lipid Accumulation by Rhodosporidium toruloides CBS 14. Microbiology (N Y) 130, 1705-1710, that reports a faster urea uptake than $NH4^+$, partly due to increased urease activity when urea is used as the nitrogen source. Consistent with a previous study, it was found that a C:N ratio of 8:1 in DMR hydrolysate media containing urea yielded the highest 3HP production after 3 days (Wehrs, et al., supra.). Significant deviation from this ratio (C:N ratio of 4 or 40) led to overall lower titers. The C:N ratio of 4:1 led to comparable final titers at day 5 in DMR hydrolysate media. However, the productivity was significantly lower in the first 4 days. Thus, in an embodiment, a range of ratios of C:N can be 2:1 to 160:1, such as, 3:1 to 40:1, or 4:1 to 10:1.

It was also found that in most of the conditions employing ammonium sulfate media, the pH dropped below the pKa of 3HP (pKa=4.5), meaning that 3HP was in the acidic form. By comparison, the pH of most of the conditions employing urea media stayed above the pKa, and thus 3HP was in the charged form. As it is generally regarded that monocarboxylic acid transport happens in the neutral form across cell membranes, the higher pH in the urea media may hinder the re-uptake of 3HP and contribute to enhanced 3HP titers. Thus, in an embodiment, a pH range of the reaction or fermentation broth can be 9.5 to 2.5, such as 8.5 to 3.5, or 7.5 to 5. Buffers may be added to the broth to maintain the pH in these ranges.

In addition, the global proteomic and metabolomic analysis also found enhanced nitrogen metabolism and increases in levels of proteins that are involved in the synthesis of 3HP in optimized media conditions. These likely have contributed to the significant increase in 3HP titers in DMR urea media.

In an embodiment, large scale processing can involve vessels on the order of thousands of liters and can utilize a method of separation and purification of 3HP by means of ion-exchange resins, activated charcoal, pH adjustment, chromatographic fractionation, liquid-liquid extraction, precipitation, or a combination thereof. Methods of separating bio-based carboxylic acids are discussed in Saboe, Patrick, et al., "In situ recovery of bio-based carboxylic acids," Green Chem., 2018, 20, 1791-1804 (Mar. 16, 2018), incorporated herein by reference.

In accordance with methods disclosed herein, yields were obtained with higher yields of 3HP than previously known. Furthermore, other optimization based on the disclosure herein could reach even yields with percent yields of stoichiometric theoretical yield of, for example, 5% to 40%, such as, e.g., 10% to 30%, or 11% to 20% by weight of theoretical yield of 3HP.

As an oleaginous yeast organism, R. toruloides is known to exhibit high flux towards the precursors of lipids, malonyl-CoA. Therefore, it was theorized that the upstream metabolic flux was not the major factor limiting 3HP titers. Due to the abundance of malonyl-CoA in R. toruloides, the focus was instead placed on optimizing the downstream pathways by alleviating the product catabolism and promoting its export.

However, in the final engineered strain (MCR-ALD6-g2945), the synthesis of malonyl-CoA appears to be a rate-limiting step, as no increase in 3HP is observed with an additional copy of MCR. Malonyl-CoA is synthesized from acetyl-CoA by acetyl-CoA carboxylase (Acc). Previously, the overexpression of Acc was found to enhance lipid production in this and other hosts, and may thus be a promising next step to further enhance titers. In addition, further engineering strategies to enhance the pool of upstream precursors, acetyl-CoA, may lead to additional improvement in 3HP titers. Finally, as R. toruloides is known to naturally divert a large pool of malonyl-CoA and its upstream metabolite acetyl-CoA towards the synthesis of carotenoids and lipids, it may also be beneficial to reduce expression of these pathways in future studies.

This study demonstrated the production of 3HP in R. toruloides. The inventors leveraged the natural high flux towards malonyl-CoA in this host and implemented functional genomics and bioinformatic analysis to identify potential genetic modifications to improve production. By reducing 3HP catabolism and promoting its export, a titer of 45.4 g/L in a 2-L fed-batch bioreactor fermentation of deconstructed lignocellulosic hydrolysate R. toruloides was produced. It is believed that further optimization may be possible, through further genetic engineering of the global metabolism to optimize the supply of key precursors, such as acetyl-CoA and malonyl-CoA. Optimization of other cofactors and identification and reduction of other bottleneck steps will likely lead to further enhanced 3HP titers and yields. This work indicates that R. toruloides is an attractive host for malonyl-CoA derived bioproducts from cheap renewable carbon feedstocks.

EXAMPLES

Example 1: Plasmids and Strains

WildType *Rhodosporidium toruloides* strain IFO0880 and its derivative with the Ku70 gene deleted were obtained from previous studies (Coradetti et al., 2018 supra; Yaegashi, J., et al., 2017, *Rhodosporidium toruloides*: a new platform organism for conversion of lignocellulose into terpene biofuels and bioproducts. Biotechnol Biofuels 10, 241, each incorporated herein by reference) and used as base strains for this study. *Aspergillus pseudoterreus* strains used in this study were used as described in Pomraning et al., 2021. Integration of Proteomics and Metabolomics Into the Design, Build, Test, Learn Cycle to Improve 3-Hydroxypropionic Acid Production in *Aspergillus pseudoterreus*. Front Bioeng Biotechnol 9, incorporated herein by reference.

Gene synthesis and plasmid construction were performed by Genscript (Piscataway, NJ). The gene encoding malonyl-CoA reductase from *C. aurantiacus* ($MCR_{Ca}$) was codon optimized for *R. toruloides* based on a custom IFO0880 codon usage table using the most frequently used codons. $MCR_{Ca}$ was cloned intact as the full-length gene under the control of the forward direction of a strong, constitutively expressed bi-directional promoter "P9" (SEQ ID NO: 7, FIG. 23) from our previous study Nora et al., 2019, A toolset of constitutive promoters for metabolic engineering of *Rhodosporidium toruloides*. Microb Cell Fact 18, 117 (available as JPUB_013271 in the Joint BioEnergy Institute's Public Registry website) incorporated by reference. Additionally, the gene was split into its N- and C-termini based on a previous publication Liu et al., 2016, supra, incorporated herein by reference, and cloned under the control of the forward and reverse directions of promoter P9, respectively, to generate strain "$MCR_{Ca\text{-}Split}$".

The $MCR_{Ca}$ expression cassettes were then introduced into *R. toruloides* by targeted integration at the CAR2 locus using LiAc transformation. The strains and plasmids used in this study and listed in Tables 1 and 2 can be found on the Agile BioFoundry Registry website where they are available upon request (Ham, et al., 2012, Design, implementation and practice of JBEI-ICE: an open source biological part registry platform and tools, Nucleic Acids Res 40, e141-e141).

TABLE 1

| Plasmid Name | Description | Registry ID |
|---|---|---|
| pPBO.041 | $MCR_{Ca}$ split into its N- and C-terminal domains under the divergent promoter | ABF_009606 |
| P9-$MCR_{Ca}$-mRuby_3HP | Plasmid expressing intact $MCR_{Ca}$ under p9 promoter | ABF_010996 |
| pPBO.078_8975_G418 | CRISPR plasmid for deleting RTO4_8975 in R. toruloides | ABF_010410 |
| pTEF1-Ady2-NAT | Ady2 expression under pTEF1 promoter | ABF_010654 |
| PGK1-rtJEN1-NAT | rtJEN1 expression under PGK1 promoters | ABF_010655 |
| pGADPHK-g2945_atKu70 | g2945 expression under GAPDH promoter | ABF_010656 |
| pTEF1K-g2945_atKu70 | g2945 expression under TEF1 promoter | ABF_010657 |
| KO 8975_HYG | Deletion of RTO4_8975 by homologous recombination | ABF_010658 |
| MCR at ALD6_8975 | Expression of $MCR_{Ca}$ under bidirectional promoter at the RT04_8975 locus | ABF_010659 |

TABLE 2

| Strain Name | Parent Strain | Plasmid(s) | Part_ID |
|---|---|---|---|
| IFO0880 (AKA WT) | N.A. | N.A. | ABF_004166 |
| IFO0880 ΔKu70 | IFO0880 | N.A. | ABF_004167 |
| $MCR_{Ca\text{-}Split}$ | IFO0880 ΔKu70 | pPBO.041 | ABF_009604 |
| WT ΔRTO4_8975 | IFO0880 | pPBO.078_RTO4_8975_G418 | ABF_010660 |
| JEN1 | $MCR_{Ca\text{-}Split}$ | PGK1-rtJEN1-NAT | ABF_010661 |
| Ady2 | $MCR_{Ca\text{-}Split}$ | pTEF1-Ady2-NAT | ABF_010662 |

TABLE 2-continued

| Strain Name | Parent Strain | Plasmid(s) | Part_ID |
| --- | --- | --- | --- |
| G-g2945 | MCR$_{Ca\text{-}Split}$ | pGADPHK-g2945_atKu70 | ABF_010663 |
| T-g2945 | MCR$_{Ca\text{-}Split}$ | pTEFIK-g2945_atKu70 | ABF_010664 |
| ALD6-g2945 | T-g2945 | KO 8975_HYG | ABF_010665 |
| MCR-ALD6-g2945 | T-g2945 | MCR at ALD6_8975 | ABF_010666 |

TABLE 3

| Sequence description | SEQ ID NO: | FIG. |
| --- | --- | --- |
| RTO4_8795 | 1 | 20 |
| Codon-optimized MCR$_{Ca\text{-}Split}$ N-terminus | 2 | 20 |
| Codon-optimized MCR$_{Ca\text{-}Split}$ C-terminus | 3 | 21 |
| Protein sequence of g2945 (3HP transporter) | 4 | 21 |
| Promoter sequence of GAPDH | 5 | 20 |
| Promoter sequence of TEF1 | 6 | 20 |

Example 2: Medium and Culture Conditions and Methods

Synthetic defined (SD) medium was made following manufacturers' guidelines with 1.7 g/L yeast nitrogen base (BD Biosciences), 0.79 g/L complete supplement mix (Sunrise Science), and 100 g/L glucose. The pH was adjusted to 7.0 with NaOH. Strains were first cultivated overnight in Yeast Extract-Peptone-Dextrose (YPD) medium (BD Difco) at 30° C. with 200 rpm shaking, which were subsequently inoculated into fresh YPD medium with a 1% (v/v) inoculum. Then the overnight cultures were inoculated into a fresh SD medium with a starting optical density at 600 nm wavelength (OD$_{600}$) measurement of 0.1. The cells were cultured for 3 days for further analysis. All productions were carried out in three or four biological replicates.

For nitrogen optimization, a single colony of MCR$_{Ca\text{-}Split}$ was inoculated into 10 mL YPD, supplemented with 100 μg/mL carbenicillin and 100 μg/mL cefotaxime. Cells were grown at 30° C. with 200 rpm shaking for 24 hrs. Cells were next cultivated in media derived from corn stover biomass which was subjected to deacetylation and mechanically refinement (DMR) of the biomass into hydrolysate according to methods disclosed in Chen et al., 2016, supra.

DMR (deacetylation and mechanical refining) processing of corn stover achieves high monomeric sugar concentrations (230 g L$^{-1}$) during enzymatic hydrolysis and high ethanol concentrations (>10% v/v) during fermentation without hydrolysate purification or concentration. Chen, et al., 2016, supra. 500 μL culture was added to 9.5 mL of 16.7% (v/v) DMR hydrolysate and mock DMR hydrolysate media with the indicated nitrogen sources and C:N ratios. DMR hydrolysate medium was made by diluting a concentrated DMR hydrolysate (see Chen et al., 2016, supra) to 100 g/L of total sugar (64.6 g/L glucose and 34.3 g/L xylose), with addition of 0.1 mM FeSO$_4$, 100 mM potassium phosphate (buffered to pH 5.6), 100 μg/mL carbenicillin, and 100 μg/mL cefotaxime. Mock hydrolysate medium is a SD medium containing the same glucose and xylose concentrations as the DMR hydrolysate medium, with addition of 0.1 mM FeSO$_4$, 100 mM potassium phosphate (buffered to pH 5.6), 0.79 g/L YNB without ammonium sulfate or amino acids, 1.7 g/L CSM, 100 μg/mL carbenicillin, and 100 g/mL cefotaxime.

Various elemental C:N ratios (by moles) were tested which includes 4:1, 8:1, 40:1 and 160:1. The nitrogen sources ammonium sulfate and urea were tested. Cells were grown at 30° C. with 200 rpm shaking for 24 hrs. OD$_{600}$ was measured and the culture was diluted for an OD$_{600}$ of 0.1 in 1 mL using a 48-well FlowerPlate (m2p-labs) with flower-shaped baffles to support mixing, and sealed with a gas-permeable sealing film (Excel Scientific Inc). Cells were grown at 30° C. with 830 rpm shaking and 70% humidity in a Multitron (Infors HT). Biological triplicates were used.

Samples were taken between days 1 and 5 and were frozen at −20° C. until further analysis. Samples were thawed, centrifuged at 1,504×g for 3 minutes, and supernatant diluted 1:20 (v/v) into water. Samples were filtered with 0.2 μm filtration at 3,220×g for 5 minutes. Sugar and 3HP were quantified via HPLC.

For minimal media experiments, minimal media was prepared using 6.7 g/L yeast nitrogen base without amino acids (BD Difco) supplemented with 0.79 g/L CSM powder (Sunrise Science Products) and adjusted to a starting pH of 6.0. This media was supplemented with either 10 g/L glucose, 0.5% (v/v) 3HP (TCI chemicals), or both.

Example 3: Transformation of R. toruloides

Heterologous DNA was introduced into the R. toruloides genome using a modified version of lithium acetate (LiAc) transformation. R. toruloides base strains were streaked onto YPD plates, individual colonies were selected, and grown in 10 mL YPD overnight at 30° C. with 200 rpm shaking. The following afternoon, cultures were diluted to an OD$_{600}$ such that they would reach an OD$_{600}$ of 0.8 the following morning, assuming a growth rate of 0.3 hr$^{-1}$. Cultures for transformation were pelleted at 4,000×g for 5 minutes and washed twice with H$_2$O and twice with 150 mM LiAc (Sigma-Aldrich). Pellets were resuspended in 240 μL 50% (wt/vol) PEG 4000 (Sigma-Aldrich), 54 μL 1.0 M LiAc, 10 μL salmon sperm DNA (Thermo Fisher), and 56 μL of transforming DNA (approximately 1 mg of plasmid DNA linearized with PvuII). Cells were incubated at 30° C. for 1 h, supplemented with 34 μL of DMSO (Sigma-Aldrich), and incubated at 37° C. for 5 min. Cells were centrifuged, washed once with YPD, and grown overnight in 2 mL YPD. Overnight cultures were plated on YPD supplemented with the appropriate antibiotic and grown for 2-3 days at 30° C.

Example 4: Analytical Methods

Cell density was measured by the absorbance at 600 nm wavelength (OD$_{600}$) (SPECTRAmax Plus, Molecular Devices). For quantification of extracellular metabolites including glucose, glycerol, xylose and 3HP, a high-performance liquid chromatography (HPLC) system (Agilent) equipped with an HPX-87H column (Bio-Rad) and a refractive index detector (RID, Agilent) was used. The autosampler, column and RID temperature were maintained at 4° C., 65° C. and 45° C., respectively. The mobile phase was 5 mM sulfuric acid solution at a flow rate of 0.6 mL/min. All samples were filtered through a 0.22 μm membrane filter (VWR centrifugal Filter) before injection of 10 μL of filtered samples.

Example 5: Deletion of 3HP Consumption Pathway

The putative gene responsible for 3HP consumption, RTO4_8975, was deleted using CRISPR-Cas9 to introduce indels causing a frameshift as was previously outlined by Otoupal et al., 2019, supra. Plasmid ABF_010410 was linearized with PvuII restriction enzyme digestion (ThermoFisher) and transformed into WT IFO0880 as described above in Example 3. Colony PCR followed by Sanger Sequencing (Azenta) was performed to identify successful frameshifts confirming successful knockout of RT04_8975.

To confirm abated 3HP consumption, wild type (WT), $MCR_{Ca-Split}$ (see Table 2), and wild type with RTO4_8975 deleted (WT ΔRTO4_8975, see Table 2) were streaked onto YPD plates and cultivated at 30° C. for 2 days. Three biological replicates of each strain were inoculated into 5 mL YPD and grown for 2 days at 30° C. with 200 rpm. Cultures were diluted 1:900 (v/v) into 1 mL minimal media containing 0.5% (v/v) 3HP and supplemented with or without 10 g/L glucose as the carbon source and cultivated for 6 days at 30° C. $OD_{600}$ measurements were sampled at day 2, and 3HP concentrations were subsequently measured as previously described at the end of the experiment.

Example 6: Bioreactor Fermentation

For bioreactor fermentations in the Ambr® 250 system, YP20D medium was made with 10 g/L yeast extract, 20 g/L Bacto-tryptone and 200 g/L glucose supplemented with 100 µg/mL carbenicillin and 100 µg/mL cefotaxime. 3HP production in $MCR_{Ca-Split}$ was examined using a fed-batch Ambr® 250 system (Sartorius A G., Goettingen, Germany). Fermentation was performed at 30° C. with agitation at 400 rpm. A lower limit pH of 5 was set, with automatic feeding of 2 N NaOH to cultures falling below this limit. Foaming was suppressed by adding 1% (v/v) antifoam in water (Antifoam 204, Sigma). 150 mL YP20D medium was inoculated with an overnight culture in YPD at an initial $OD_{600}$ of 0.1. Culture samples of 2 mL were collected at a series of time points every 24 hrs to monitor cell density, sugar consumption, and 3HP and glycerol production. A 600 g/L glucose solution was used to bring up glucose concentrations to 50 g/L at day 3 and day 4 when they were exhausted in the medium.

For 3HP production in the fed-batch 2 L bioreactor, MCR-ALD6-g2945 strain was inoculated in YPD with two antibiotics (100 µg/mL carbenicillin and 50 µg/mL hygromycin B) and grown for 2 days. For the adaptation, the overnight culture was inoculated 1% (v/v) into fresh 5 mL 50% (v/v) diluted modified DMR8U medium and grown overnight. The final seed culture was inoculated into a 250 mL baffled flask containing 50 mL 50% (v/v) diluted modified DMR8U medium at 30° C. and 200 rpm for 12 h. The cell culture was inoculated at an initial $OD_{600}$ of 1.0 in a 2 L bioreactor (Biostat B, Sartorius, Germany) containing IL modified DMR8U medium.

The modified DMR8U medium contains DMR hydrolysate with 120 g/L total sugar, 16 g/L urea. 10.7 g/L $K_2HPO_4$, 5.2 g/L $KH_2PO_4$, 10 mM $MgCl_2$, 1 mL of trace metal solution, 1 mL of vitamin solution and antibiotics (100 µg/mL carbenicillin and 50 µg/mL hygromycin B). The trace metal solution contained: 4.5 g/L $CaCl_2 \cdot 2H_2O$, 4.5 g/L $ZnSO_4 \cdot 7H_2O$, 3 g/L $FeSO_4 \cdot 7H_2O$, 1 g/L $H_3BO_3$, 1 g/L $MnCl_2 \cdot 4H_2O$, 0.4 g/L $Na_2MoO_4 \cdot 2H_2O$, 0.3 g/L $CoCl_2 \cdot 6H_2O$, 0.1 g/L $CuSO_4 \cdot 5H_2O \cdot 0.1$ g/L KI, and 15 g/L EDTA. The vitamin solution contained 50 mg/L biotin, 200 mg/L 4-aminobenzoic acid, 1 g/L nicotinic acid, 1 g/L Ca-pantothenate, 1 g/L pyridoxine-HCl, 1 g/L thiamine-HCl, and 25 g/L myo-inositol. (Kim, Joonhoon, et al., 2021, Multi-Omics Driven Metabolic Network Reconstruction and Analysis of Lignocellulosic Carbon Utilization in *Rhodosporidium toruloides*. Front Bioeng Biotechnol 8, incorporated herein by reference.)

The dissolved oxygen (DO), airflow, and temperature were set to 30%. 2 VVM (volume of air per volume of liquid per minute), and 30° C. respectively. The pH was left uncontrolled. To produce 3HP in the fed-batch fermentation. 600 g/L glucose feeding stock solution was added manually when the residual glucose concentration dropped below 20 g/L in the medium to maintain 50-100 g/L glucose in the medium. The residual glucose was measured using a glucose meter (CVS Health) and HPLC as described previously (Kim, et al, 2021, supra).

Example 7: Proteomic and Metabolomic Analysis

Samples for differentially expressed metabolites were collected during the Ambr® 250 run. Briefly, six $OD_{600}$ samples were taken on day 1 and day 4, washed once with water and pelleted for 5 minutes at 4,000 rpm. Strains to explore metabolic shifts in different nitrogen sources were cultured in 48-well FlowerPlates. Six $OD_{600}$ samples were also collected on day 3 and day 5, washed once with water and pelleted for 5 minutes at 4,000 rpm. All cell pellets were flash frozen with liquid nitrogen and stored at −80° C. until further analysis. Extraction of metabolites and proteins, as well as global proteomic and metabolomic analysis were performed with methods published in previous studies (Kim, Joonhoon, et al., 2021, Multi-Omics Driven Metabolic Network Reconstruction and Analysis of Lignocellulosic Carbon Utilization in *Rhodosporidium toruloides*. Front Bioeng Biotechnol 8, incorporated herein by reference.)

Example 8: Fitness Analysis with RB-TDNASEQ

Fitness analysis was performed as described in Coradetti, et al., 2018, supra, incorporated herein by reference. Briefly, three aliquots of the random insertion mutant pool of *R. toruloides* were thawed on ice and recovered in 100 mL YPD (BD Difco, 242820) for two generations ($OD_{600}$ 0.2 to $OD_{600}$ 0.8). 10 mL of each starter culture was pelleted and frozen as an initial "time 0" sample. The remaining cells were pelleted 5 minutes at 4,000 RCF, washed twice with water and inoculated at $OD_{600}$ 0.1 in 50 mL SD media with or without 76 mM $KH_2PO4$ (Sigma Aldrich) and 24 mM $K_2HPO4$ (Sigma Aldrich), supplemented with 1% (w/v) carbon source at pH 5.0 to 7.0 (as indicated). Cultures were grown to $OD_{600}$ between 5 to 10 (approximately 20 to 50 hrs depending on carbon source) at 30° C., 200 rpm in baffled flasks (DWK Life Sciences). 10 mL samples were pelleted and frozen for DNA extraction. DNA extraction, barcode amplification, and sequencing was performed as described in Kim et al., 2021, supra.

Example 9: Construction of 3HP Biosynthesis Pathway in *R. toruloides*

The malonyl-CoA to 3HP pathway was focused on because *R. toruloides* is oleaginous and has a relatively high flux towards malonyl-CoA. The malonyl-CoA reductase was codon optimized and expressed from *Chloroflexus aurantiacus* ($MCR_{Ca}$) using two approaches. First, $MCR_{Ca}$ was expressed intact under control of the forward orientation of a strong, constitutive, and bi-directional promoter previously characterized by Nora et al, 2019, supra. Seeond, to balance the enzyme activities of $MCR_{Ca}$, the $MCR_{Ca}$ gene encoding the N-terminal and C-terminal portions of the protein (MCR$_{Ca\text{-}Split}$) was split and these were expressed separately under both orientations of this promoter (Liu et al., 2016) (FIG. 4).

Figure 4:
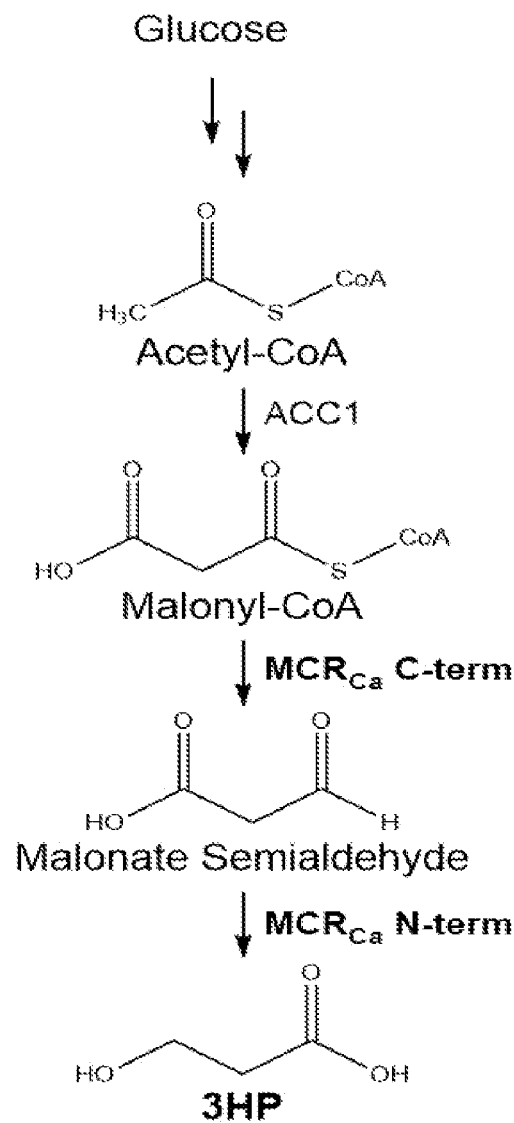
FIG. 4 is a schematic for 3HP production via the malonyl-CoA pathway in *R. toruloides*.
Figure 5:
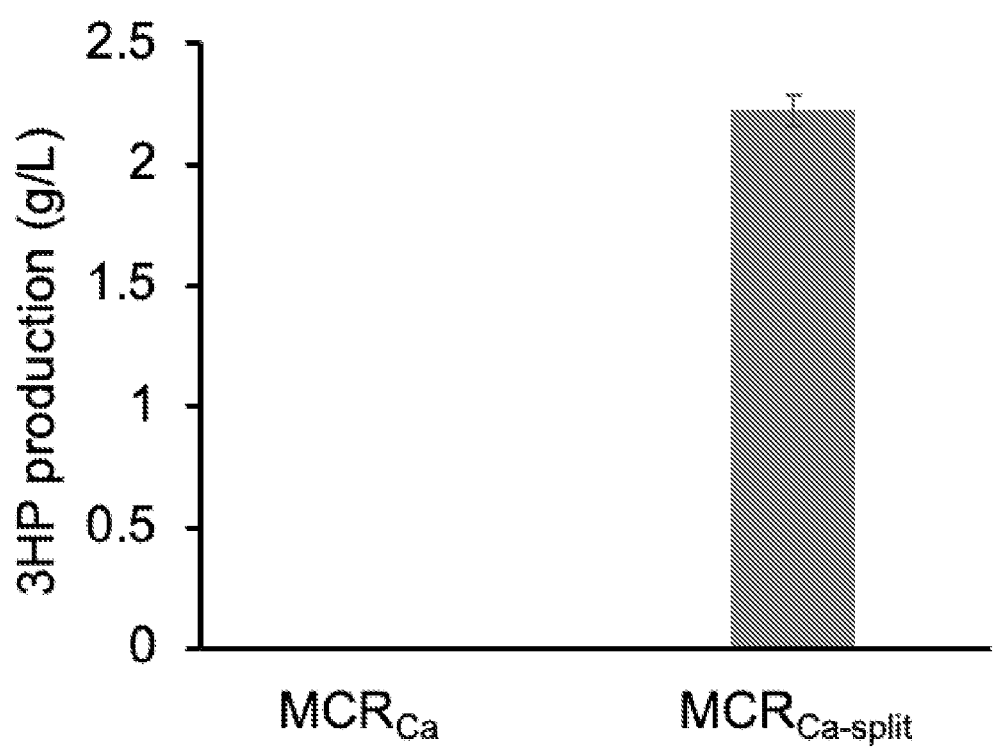
FIG. 5 is a graph showing 3HP production from the malonyl-CoA pathway in test tubes cultured in SD medium.
Figure 6:
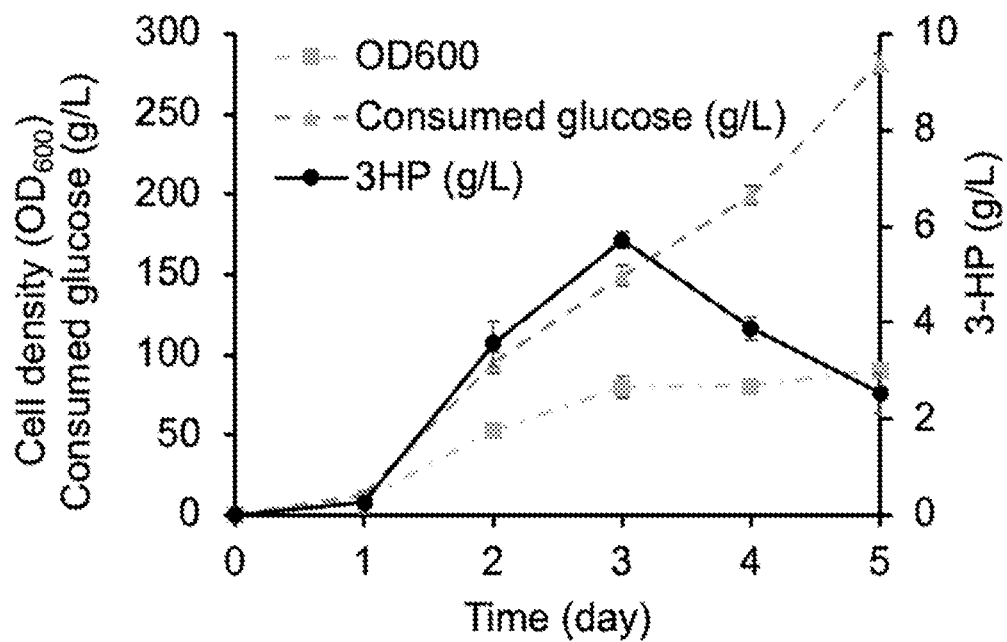
FIG. 6 is a graph showing 3HP production in Ambr® 250 bioreactor cultured in YP20D media.

FIG. 4 shows the schematic and results of 3HP production via the malonyl-CoA pathway in R. toruloides. FIG. 4 shows the reactions performed by the bifunctional enzyme, malonyl-CoA reductase from C. aurantiacus (MCR$_{Ca}$), causes a split into the N- and C-terminal components. FIG. 5 shows 3HP production from malonyl-CoA pathway in test tubes cultured in SD medium. All error bars represent standard deviations of biological triplicates. FIG. 6 shows 3HP production in Ambr® 250 bioreactor cultured in YP20D media. Error bars represent standard deviation from triplicate runs.

LiAc transformations were performed to integrate the cassettes into the CAR2 locus of R. toruloides for the robustness of integration and ease of screening at this locus, selected three transformants of each construct, and cultured the strains in SD medium (10% glucose) for three days in test tubes. Extracellular supernatant was then collected and analyzed via HPLC to screen for 3HP production. The strain harboring the MCR$_{Ca\text{-}Split}$ gene produced 2.2±0.1 g/L 3HP, while that harboring the intact MCR$_{Ca}$ gene failed to yield any measurable 3HP (FIG. 5). The results, together with others' observations (Liu, et al., 2016, supra), collectively indicate the importance of individually expressing and balancing the two functional domains of MCR$_{Ca}$.

The strain successfully producing 3HP was titled "MCR$_{Ca\text{-}Split}$". To test the scalability of this process, an Ambr® 250 run was performed. After 5 days of cultivation, the culture reached an OD$_{600}$ of 90.3 and 3HP production peaked on the 3rd day at 5.7 g/L, corresponding to a yield of 0.04 g 3HP/g glucose (FIG. 6).

The majority of cell growth happened on the first three days, reaching 88.3% of its maximum. Although cell growth and 3HP production dramatically slowed down or dropped after day 3, glucose consumption continued to steadily increase, which might be attributed to providing the maintenance energy of the cells. A significant drop in 3HP titer was observed from day 4, indicating R. toruloides can efficiently catabolize 3HP and may be stuck in a futile cycle of 3HP production and catabolism.

Figure 7:
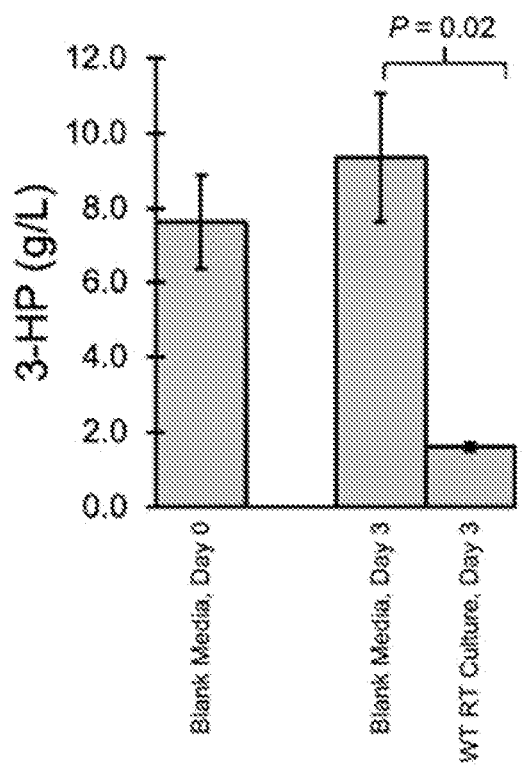
FIG. 7 is a graph showing cell growth of WT in minimal media supplemented with 3HP as the sole carbon source.

Example 10: Addressing 3HP Catabolism in R. toruloides; Identification and Deletion of Genes Involved in 3HP Catabolism To confirm 3HP could be consumed, WT R. toruloides was grown in minimal media spiked with 8 g/L 3HP. Over the course of three days, no reduction in 3HP was observed in blank media (9.3±1.7 g/L) (FIG. 7). However, media inoculated with R. toruloides had only 1.6±0.1 g/L 3HP, significantly lower than the blank media (P=0.02). This shows that R. toruloides is capable of catabolizing 3HP.

To better understand the consumption of 3HP by R. toruloides, RB-TDNA sequencing was performed on R. toruloides grown with 3HP or various other carbon sources. A pooled library of R. toruloides variants with barcoded sequences randomly integrated into the genome (Coradetti, et al. 2018, supra, incorporated herein by reference) was grown for 3 days. Barcodes which were significantly underrepresented during growth on a particular carbon source are indicative of the genetic loci of potential genes associated with consumption of that carbon source.

Figure 2:
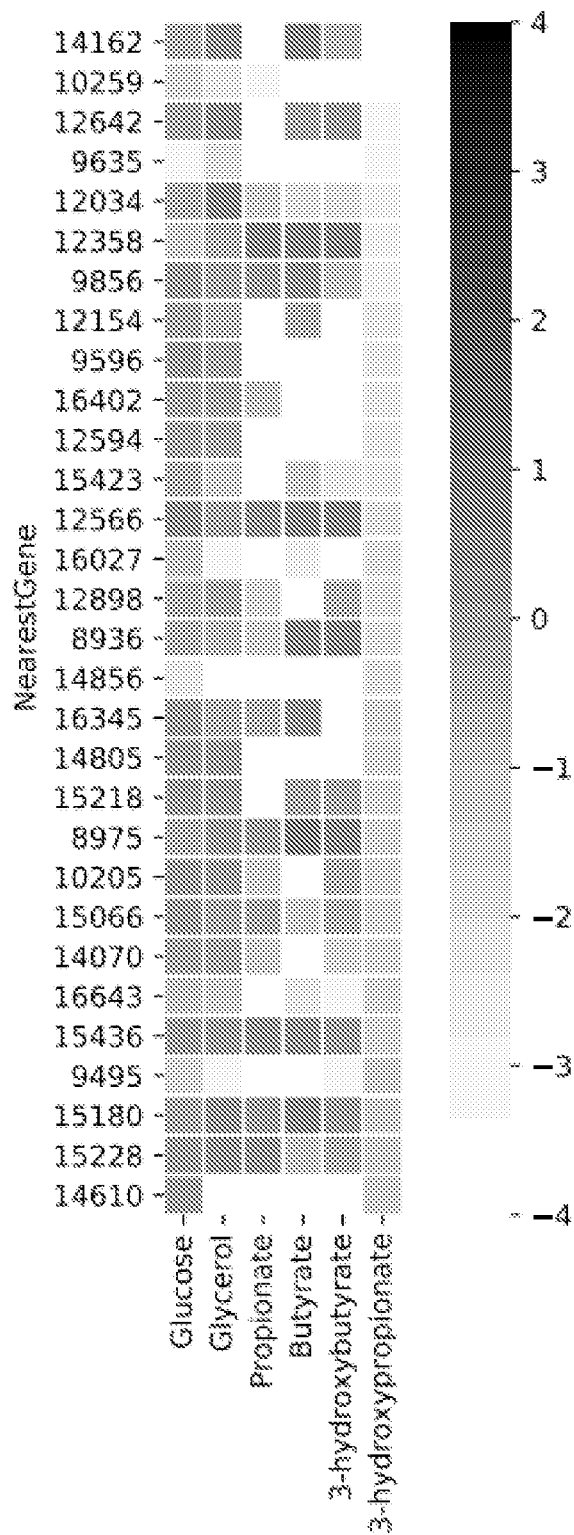
FIG. 2 is a plot of fitness scores of potential genes involved in 3HP catabolism.

The top 100 genes that showed fitness defects in 3HP were selected, out of which 30 genes were directly involved in metabolic pathways and were ranked based on their fitness defects in 3HP (FIG. 2). Among these 30 genes, about half of the genes also exhibit significant fitness defects in propionate, butyrate and 3-hydroxybutyrate, which suggest that these genes are likely involved in general short chain acid metabolism and not specific for 3HP. A correlation between these fitness values and those obtained during growth on either valine or leucine as the primary carbon source was observed. This was indicative of a potential link between catabolism of 3HP and branched chain amino acid metabolism in R. toruloides. This link between 3HP and branched-chain amino acid catabolism has also been previously reported in Cupriavidus necator. (Arenas-López et al., 2019, The genetic basis of 3-hydroxypropanoate metabolism in Cupriavidus necator H16. Biotechnol Biofuels 12, 150.)

One of the genes identified in this library, RTO4_8975, was notable. It was previously reported that deletion of the putative malonate semialdehyde dehydrogenase gene, Apald6, abated 3HP consumption by the fungus Aspergillus pseudoterreus (Pomraning et al., 2021), supra. The protein encoded by RTO4_8975 shares 56% protein sequence homology with this gene. Deletion of the RTO4_8975 gene was performed by employing the recently developed CRISPR-Cas system (Otoupal, et al., 2019, supra).

Figure 8:
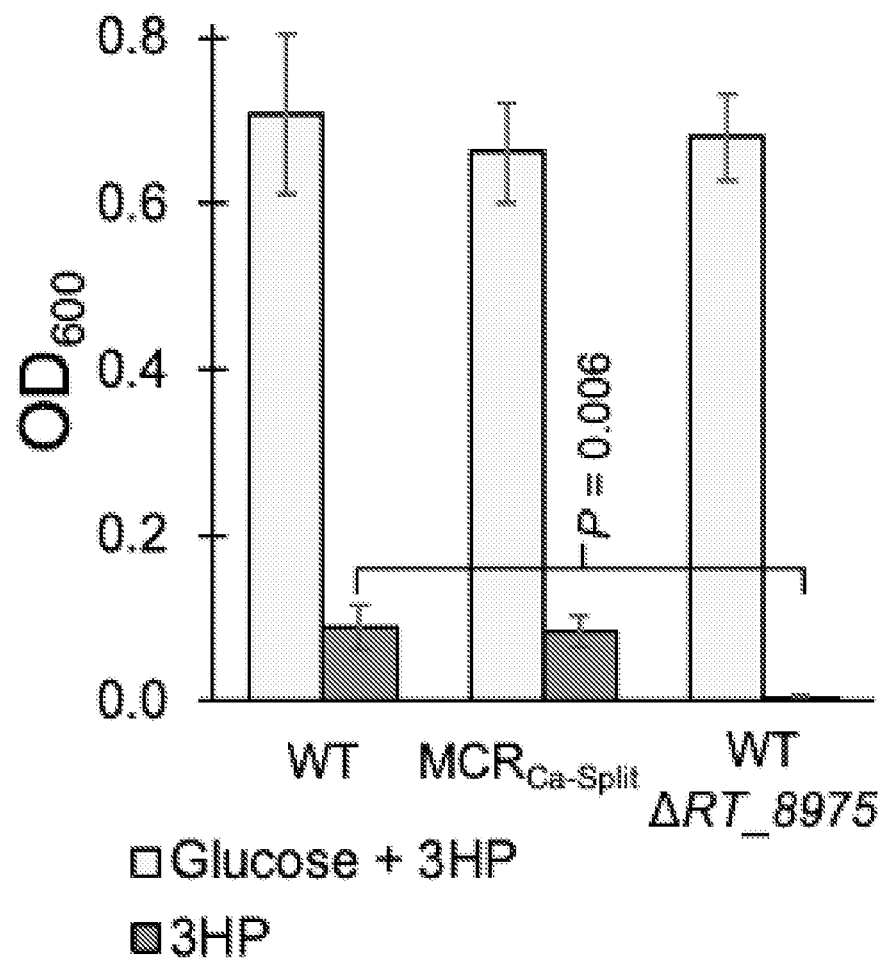
FIG. 8 is a graph showing growth of WT, $MCR_{Ca-Split}$, and WT with RTO4_8975 deleted in minimal media supplemented with glucose and 3HP, or 3HP as the sole carbon source.
Figure 9:
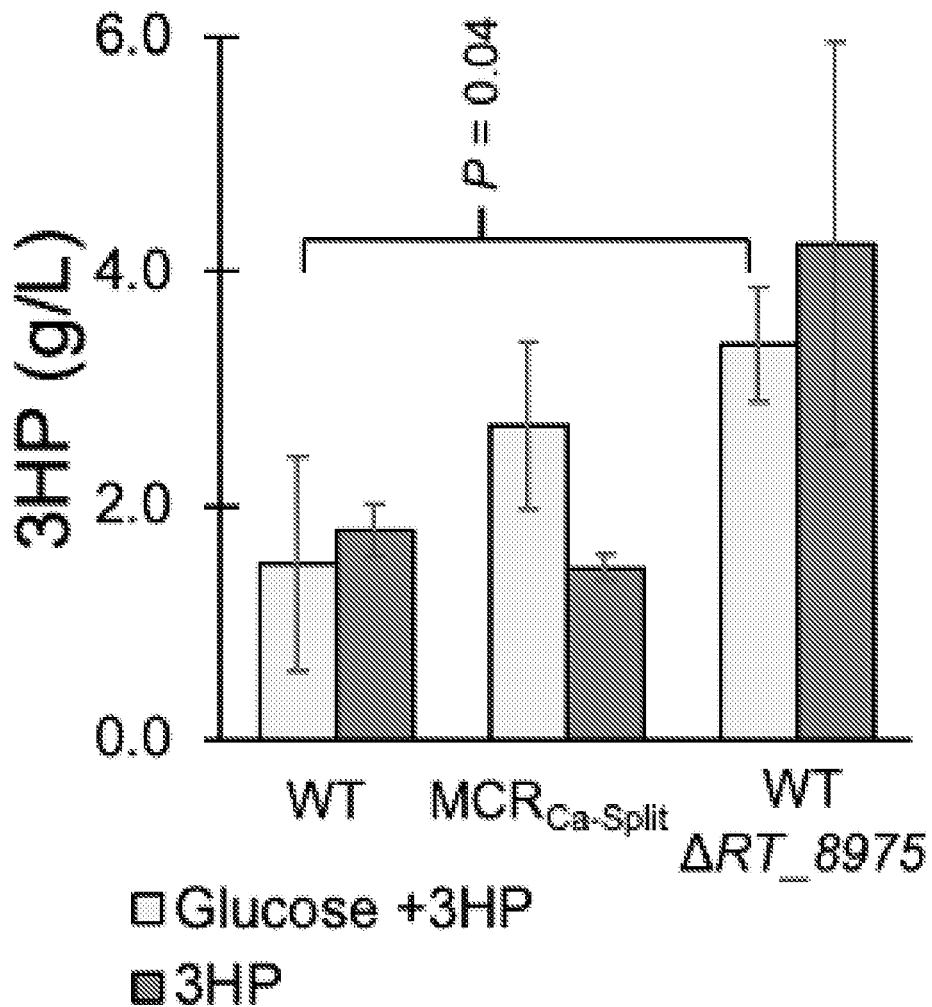
FIG. 9 is a graph showing titers of remaining (or produced) 3HP in minimal media cultures. All P-values were calculated using a two-tailed type II Student's t-test.

Sanger sequencing confirmed a 13 bp indel near the cut site, causing a frame-shift and effectively eliminating the expression of this gene. This deletion caused no impact on growth in a mixed glucose-3HP minimal media (FIG. 8). However, with 3HP as the sole carbon source, growth was significantly hindered (P=0.006) relative to WT R. toruloides (FIG. 8). Additionally, significantly (P=0.04) greater 3HP remained after cultivation in the WT ΔRTO4_8975 strain (FIG. 9). This further confirms the role of this putative malonate semialdehyde dehydrogenase in catabolism of 3HP. RTO4_8975 is the gene ID number in the public database and ALD6 the protein that this gene (RTO4_8975) encodes.

The R. toruloides gene RTO4_8975, annotated as an aldehyde dehydrogenase, was identified from RB-TDNAseq and deleted in the WT using CRISPR-Cas9, and compared against WT and MCR$_{Ca\text{-}Split}$ strains for its ability to consume 3HP in minimal media.

Example 11: Engineering 3HP Transporter in R. toruloides

After preventing 3HP consumption by deleting catabolic genes, efforts were focused on improving production of 3HP by enhancing its export outside of the cell. The metabolomic analysis of MCR$_{Ca\text{-}Split}$ indicates that there was intracellular accumulation of 3HP (See FIG. 3). This suggested that engineering enhanced 3HP transport to facilitate the export of 3HP from the cell may improve 3HP titers.

Transporters previously characterized and reported in the literature for monocarboxylic acids with similar chemical structures to 3HP, such as lactic acid and propionic acid were investigated. Two R. toruloides monocarboxylic acid transporters were expressed that are homologous to two characterized lactic acid transporters in S. cerevisiae, Ady2 (RTO4_10658) and JEN1 (RTO4_10184) under the control of a pTEF1 and pPKG1 promoter, respectively. A candidate 3HP transporter from Aspergillus pseudoterreus was also investigated. Global proteomics data from A. pseudoterreus strains that produce 3HP was compared with non-producer strains see (Pomraning et al., 2021, supra) to identify transporters that were upregulated in producer strains. Also, transcriptome data from a non-producer strain growing with 3HP as the sole carbon source or with 3HP spiked into production medium was compared with unspiked controls to identify 3HP responsive genes (FIG. 10).

From this analysis, g2945 (jgi|Asppseute1|473891) was identified as a 3HP responsive MFS monocarboxylate transporter that may be involved in 3HP transport across the plasma membrane of A. pseudoterreus. Notably, this transporter is upregulated in strains that accumulate 3HP intracellularly as well as in conditions where extracellular 3HP is metabolized, suggesting transport may be bidirectional and dependent on the concentration gradient of 3HP and any coupling ions involved.

Figure 10:
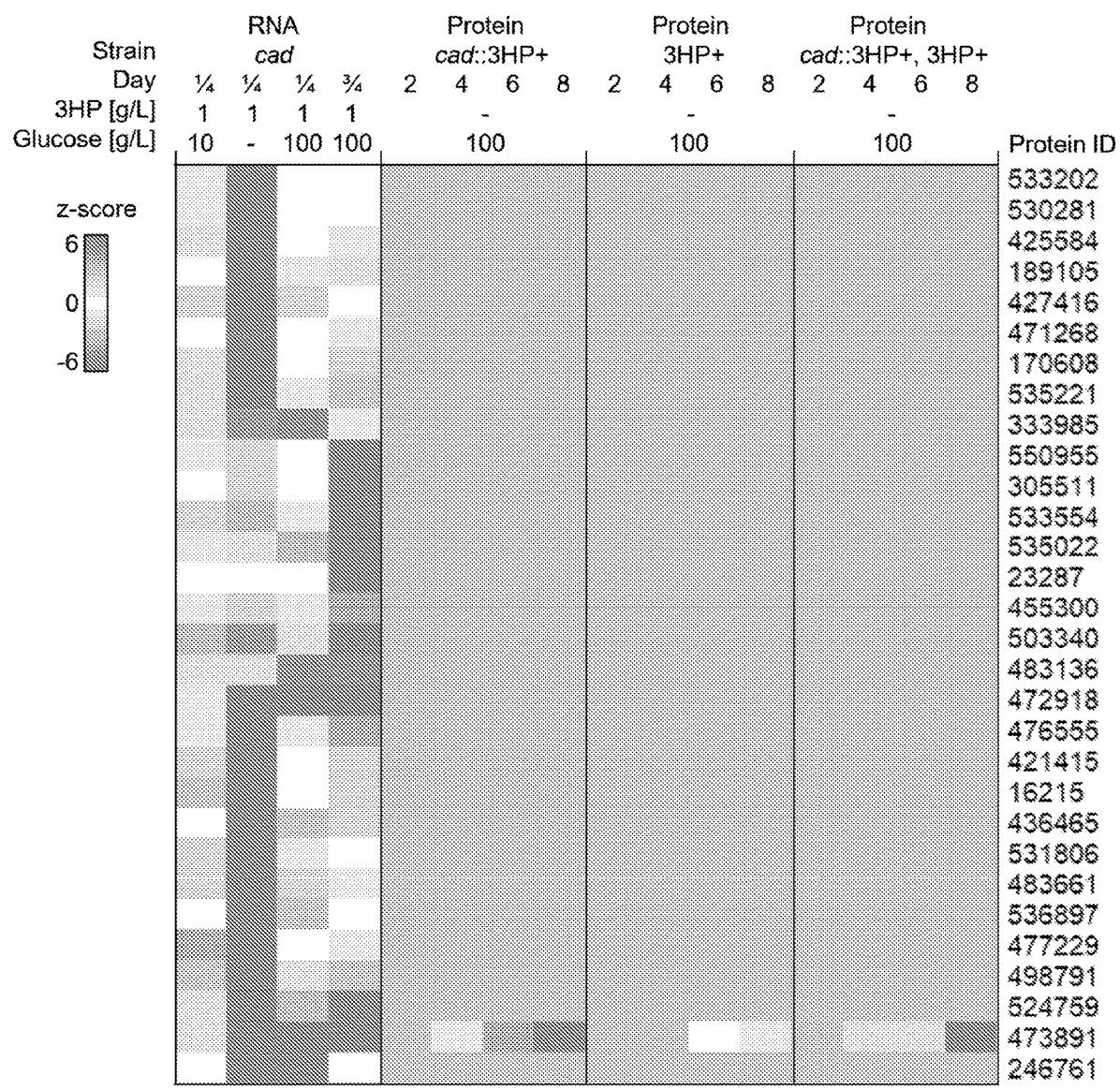
FIG. 10 is a plot showing 3HP responsive MFS transporters in *Aspergillus pseudoterreus*.

FIG. 10 is a plot showing 3HP responsive MFS transporters in Aspergillus pseudoterreus. A non-3HP producing A. pseudoterreus strain was examined by RNA-seq for genes that increase in expression level in response to spiked 3HP present as a sole carbon source or in production conditions. Z-scores indicate change versus conditions without spiked 3HP. 3HP producing A. pseudoterreus strains were examined by proteomics for genes that increase in expression level in response to the presence of the 3HP production pathway. Z-scores indicate change versus unengineered parental strains. The 30 MFS transporters with the highest average increase in expression level across the datasets are shown. The MFS transporter g2945 (jgi|Aspp-seute1|473891) was chosen for overexpression. cad::3HP+, 3HP+ and cad::3HP+, 3HP+ are three previously developed 3HP producing A. pseudoterreus strains See Pomraning, et al., 2021, supra.

The transporter g2945 was codon optimized under the control of two commonly used R. toruloides promoters, pGAPDH and pTEF1, and expressed at the Ku70 locus in the $MCR_{Ca\text{-}Split}$ strain. After 3 days of cultivation in SD medium, the Ady2 and JEN1 overexpression strains did not exhibit any changes in 3HP titers compared to the parent strain whereas a significant increase in 3HP production was observed with g2945 overexpression (FIG. 4). Compared to the parent $MCR_{Ca\text{-}Split}$ strain that produces 2.0±0.08 g/L 3HP, the g2945 overexpression strain yielded 5.4±0.16 g/L and 9.2±0.08 g/L 3HP with the pGAPDH and pTEF1 promoters, respectively.

This confirmed the hypothesis that 3HP export was a rate-limiting step in the $MCR_{Ca\text{-}Split}$ strain. In addition, the previous transcriptomic and GFP expression results suggest that pTEF1 was a stronger promoter than pGAPDH (Nora, et al., 2019, supra), which further supported that 3HP production was facilitated by enhanced transport.

Figure 11:
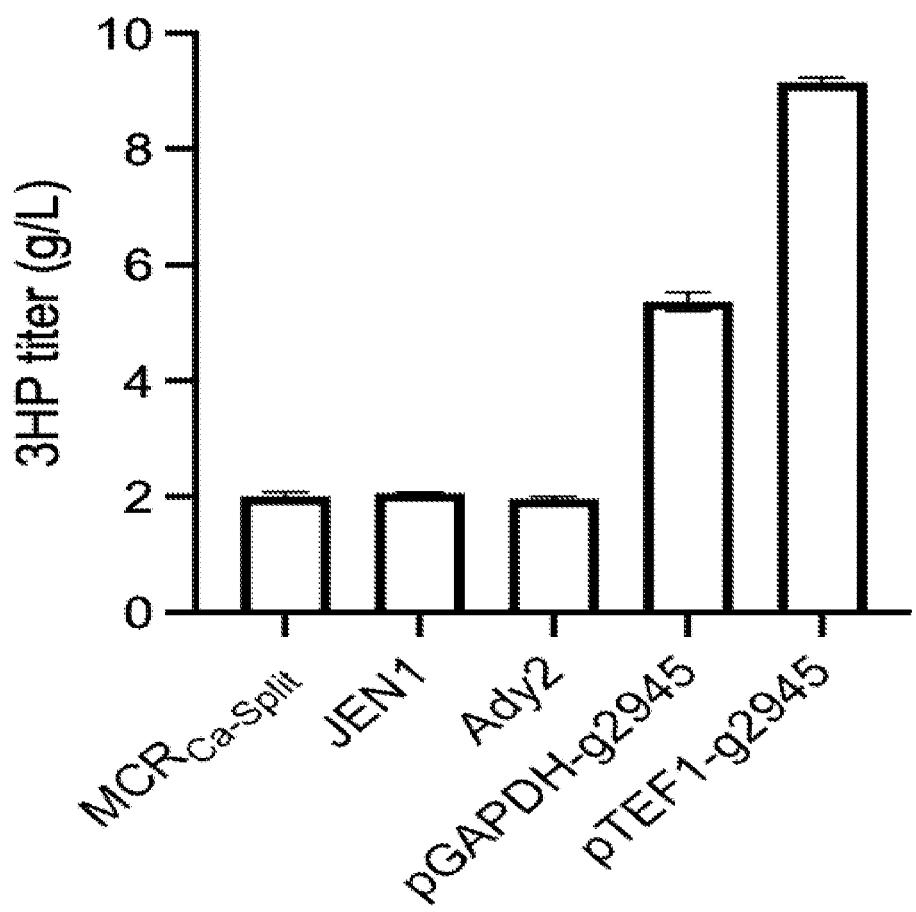
FIG. 11 is a graph showing the 3HP titers of samples with transporter engineering in *R. toruloides*. Error bars represent standard deviation of biological triplicates.
Figure 12:
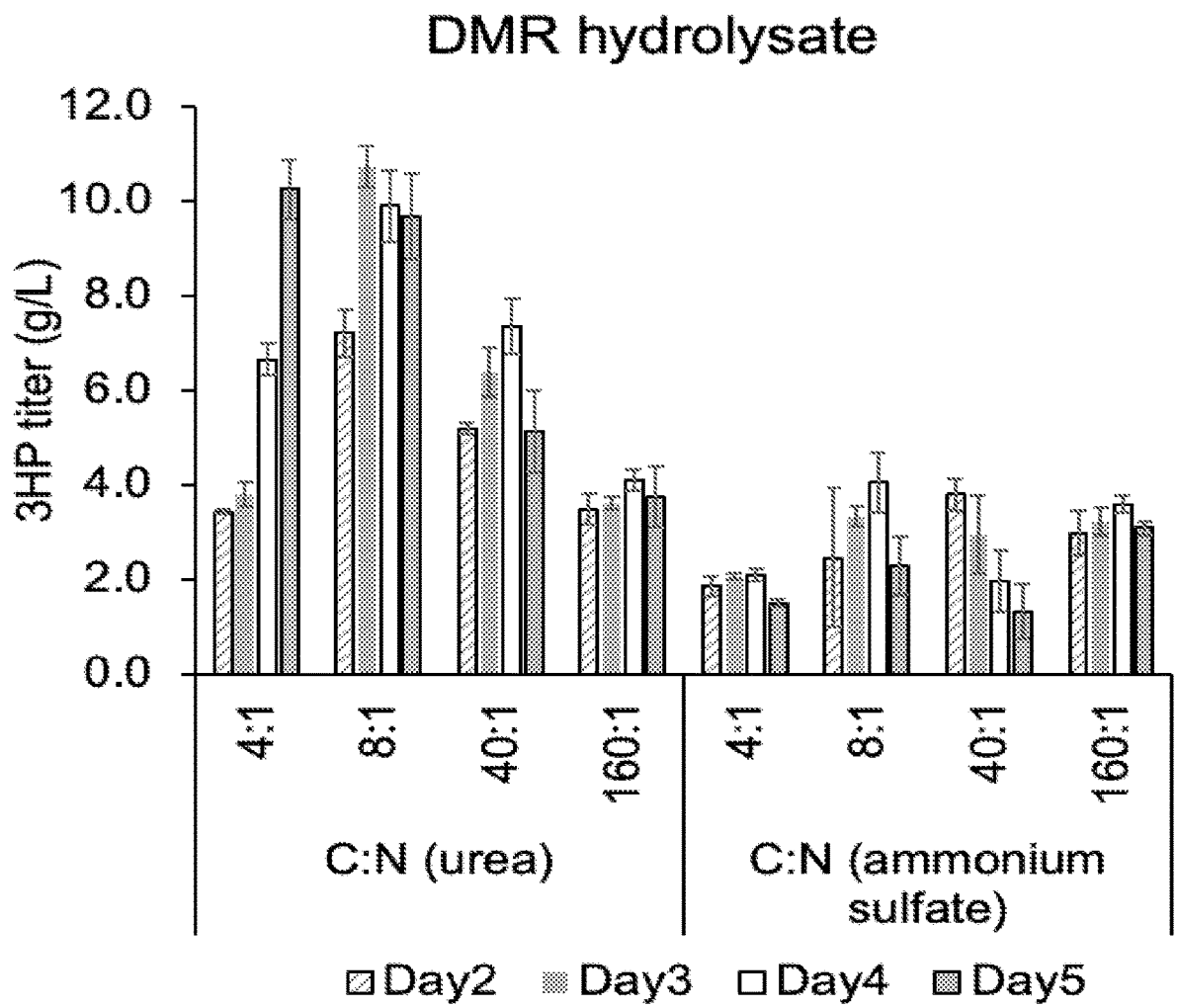
FIG. 12 is a graph showing test results with media optimization in DMR hydrolysate to enhance 3HP titers in the $MCR_{Ca-Split}$ strain.

FIG. 11 is a graph showing the 3HP transporter engineering in R. toruloides. Two R. toruloides transporters homologous to reported monocarboxylic acid transporters in S. cerevisiae, JEN1 and Ady2, were overexpressed in $MCR_{Ca\text{-}Split}$. In addition, a predicted 3HP transporter in A. pseudoterrus, g2945, was expressed under the pGAPDH and pTEF1 promoters in $MCR_{Ca\text{-}Split}$. Error bars represent standard deviation of biological triplicates.

Example 12: Medium Optimization to Enhance 3HP Production in R. truloides

Alongside genetic engineering approaches, process optimization has shown to be important in optimization of bioproduct titers, rates and yields in R. toruloides. As it is technoeconomically and environmentally favorable to produce bioproducts from lignocellulosic hydrolysate, here there was a focus on media optimization of a hydrolysate developed by deacetylation and mechanical refining (DMR) processing of corn stover biomass (denoted as DMR hydrolysate) and a mock hydrolysate that contains similar levels of glucose and xylose (denoted as mock hydrolysate). It has been established that different nitrogen sources and C:N ratios lead to significant global metabolic shifts in R. toruloides, which can lead to very different flux towards bioproducts.

Figure 13:
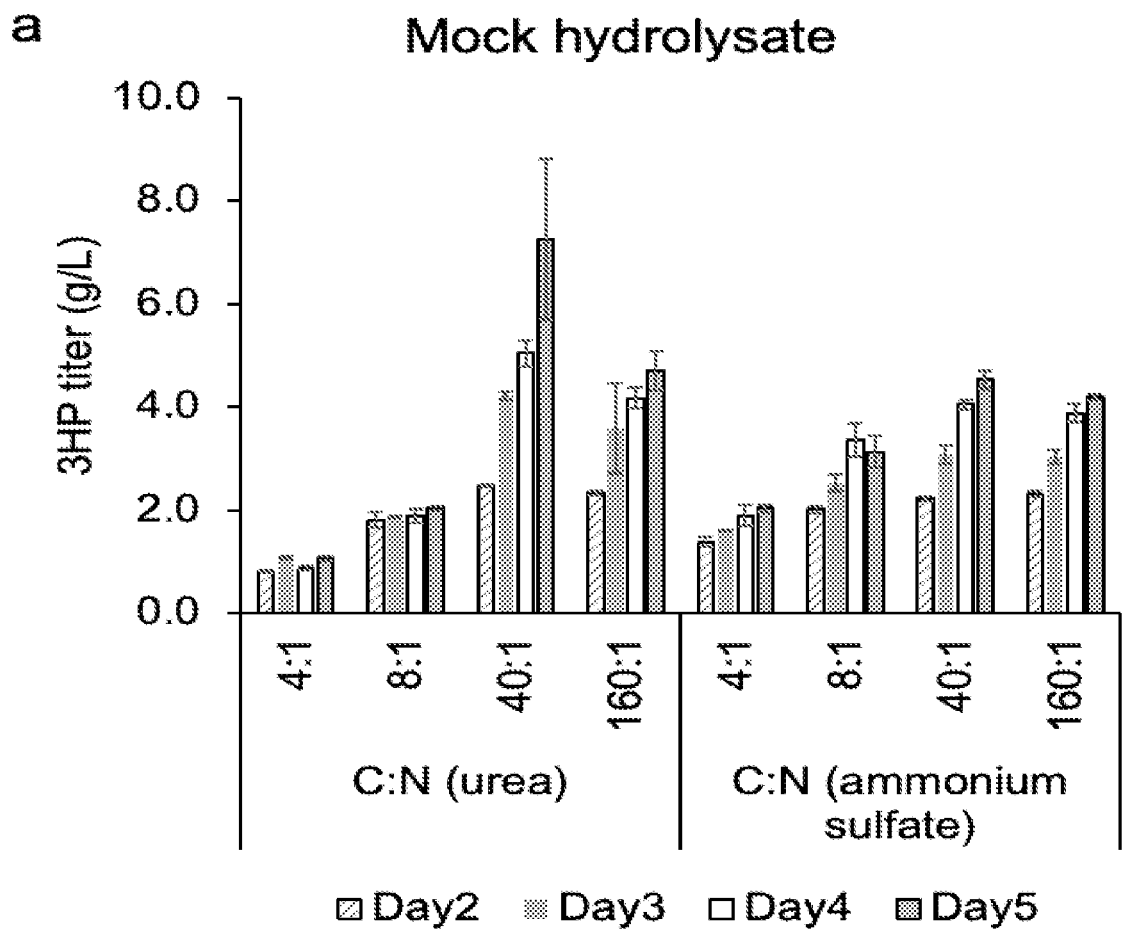
FIG. 13 is a graph showing test results with media optimization in mock hydrolysate to enhance 3HP titers in the $MCR_{Ca-Split}$ strain.
Figure 14A:
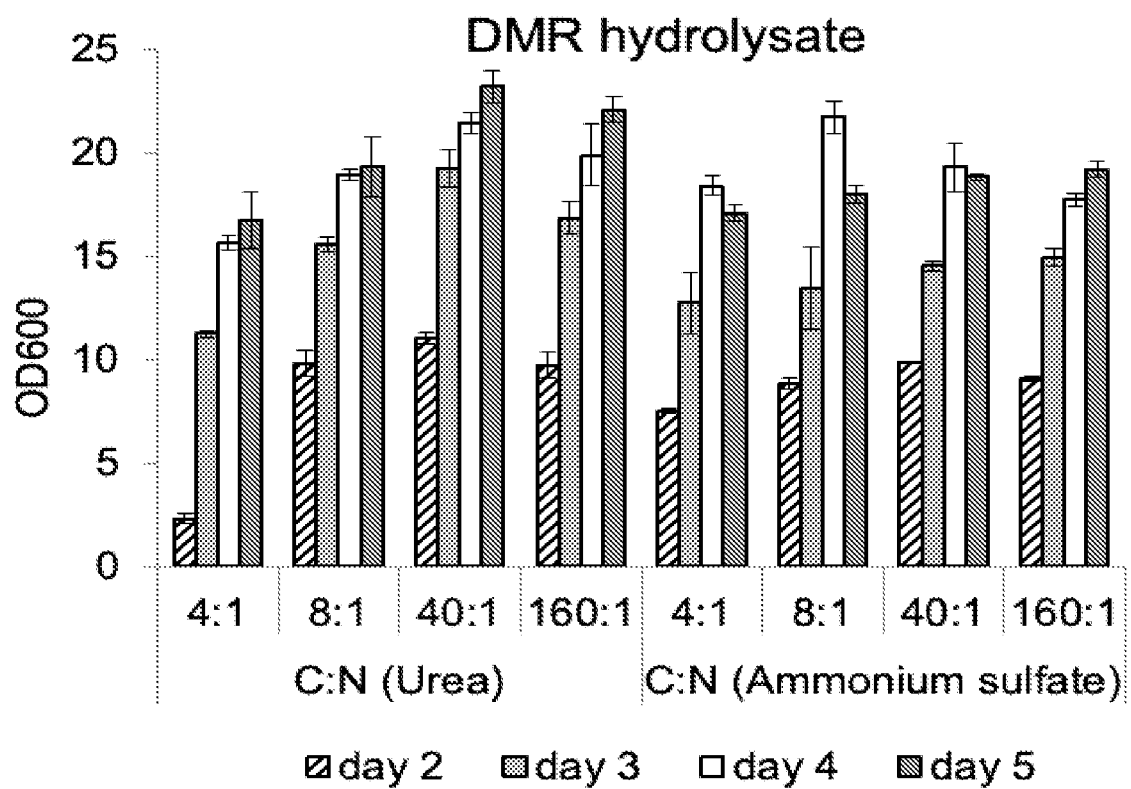
FIGS. 14A to 14D are sets of graphs showing cell growth and pH of $MCR_{Ca-Split}$ in DMR hydrolysate and mock hydrolysate.
Figure 14B:
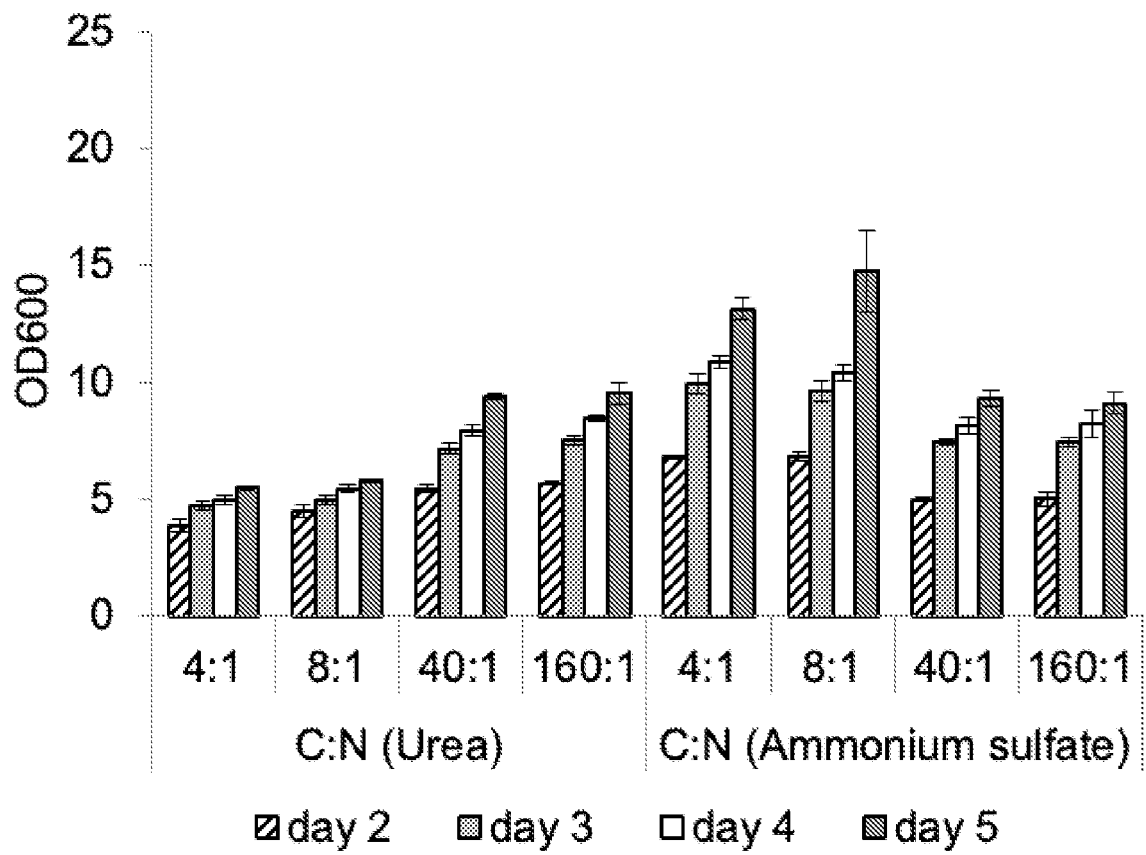
Figure 14C:
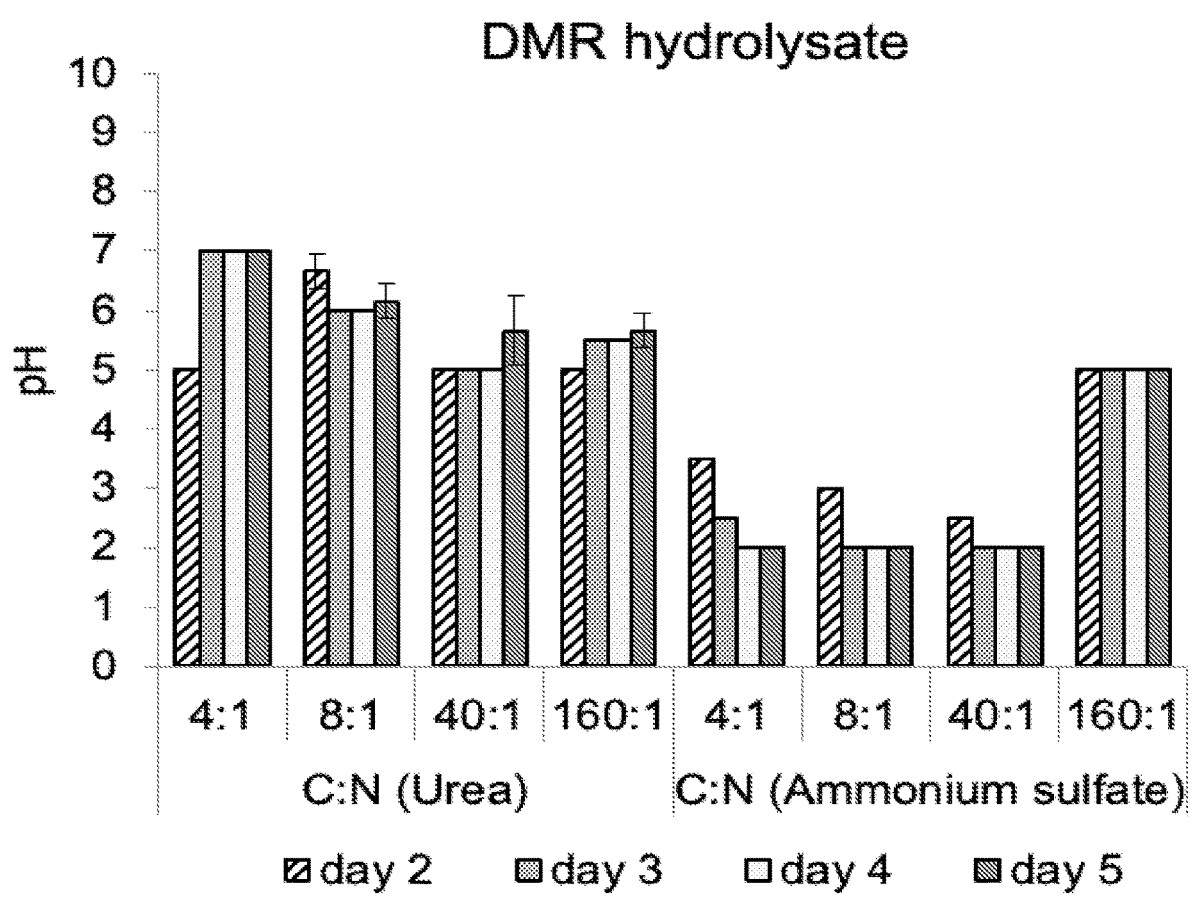
Figure 14D:
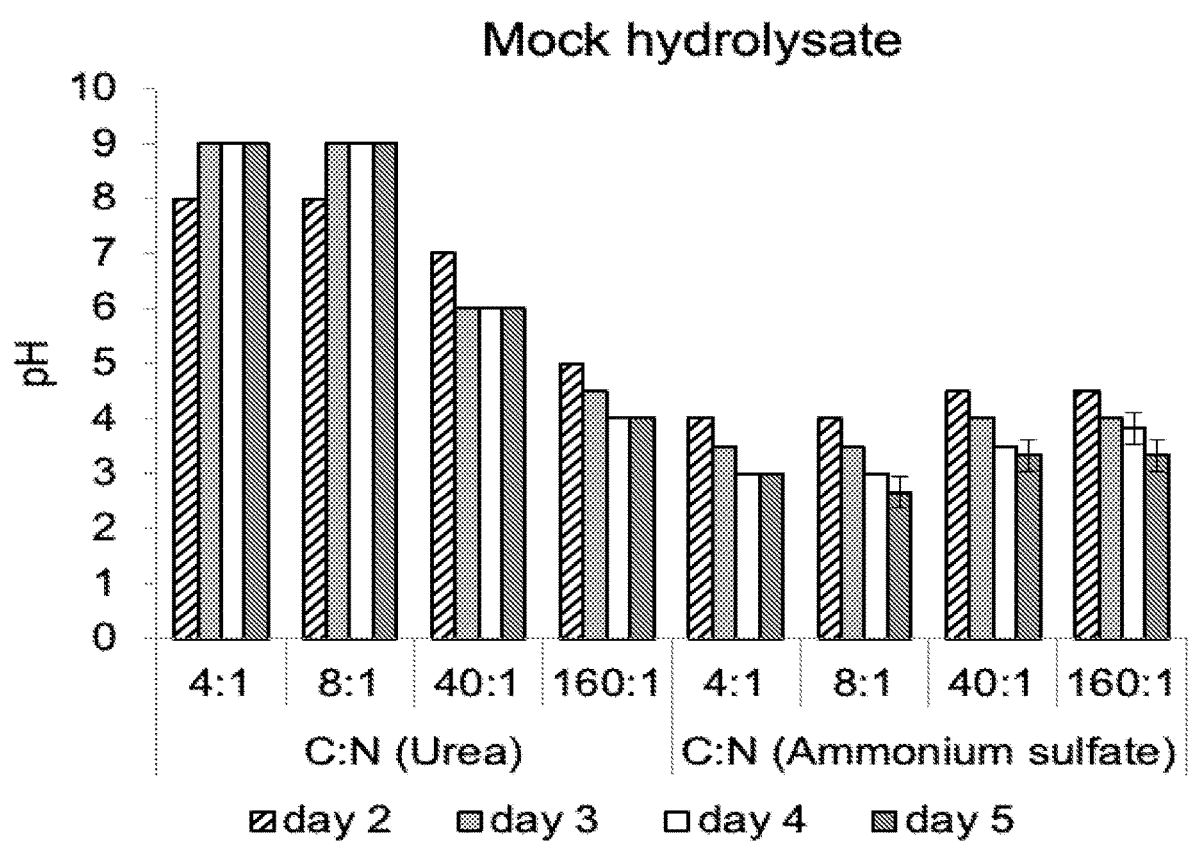

FIG. 13 shows test results of media optimization to enhance 3HP titers in the $MCR_{Ca\text{-}Split}$ strain. The $MCR_{Ca\text{-}Split}$ strain was used with two different nitrogen sources, ammonium sulfate and urea. The C:N ratios were varied at 4, 8, 40, and 160. In the mock hydrolysate medium (FIG. 13), an increase in 3HP titers was observed with increase in C:N ratios in both nitrogen sources. The highest 3HP titer reached 7.3 g/L with urea as the nitrogen source at a C:N ratio of 40. In the DMR hydrolysate medium, compared to ammonium sulfate, urea conditions exhibited significantly higher 3HP titers at all C:N ratios tested At an 8:1 C:N ratio, the 3HP titer reached 10.7 g/L, which represents a 4.8-fold increase from the initial medium condition. Cell growth measurement at OD 600 showed similar biomass accumulation in urea at C:N ratio 4:1 and 8:1 compared to other nitrogen conditions in DMR medium (FIGS. 14A-D), which indicates the differences in 3HP titers that were observed are not caused by differences in cell growth.

Interestingly, significant drops in pH were observed for most of the ammonium sulfate conditions to as low as pH 2.0 (FIGS. 14A-D), e.g., 2.5 to 6.5, 3 to 5.5, or 3.5 to 5, whereas most of the urea conditions stayed at higher pH (between pH 5.0-9.0, e.g., 5.5 to 8, or 6 to 7.5). The higher pH under urea conditions is likely caused by the assimilation of urea by urease, where two $NH_3$ molecules are released, thus increasing the pH. Based on these results, the DMR hydrolysate with urea was selected with an 8:1 C:N ratio (denoted as DMR8U media) for further strain engineering efforts.

Figure 15:
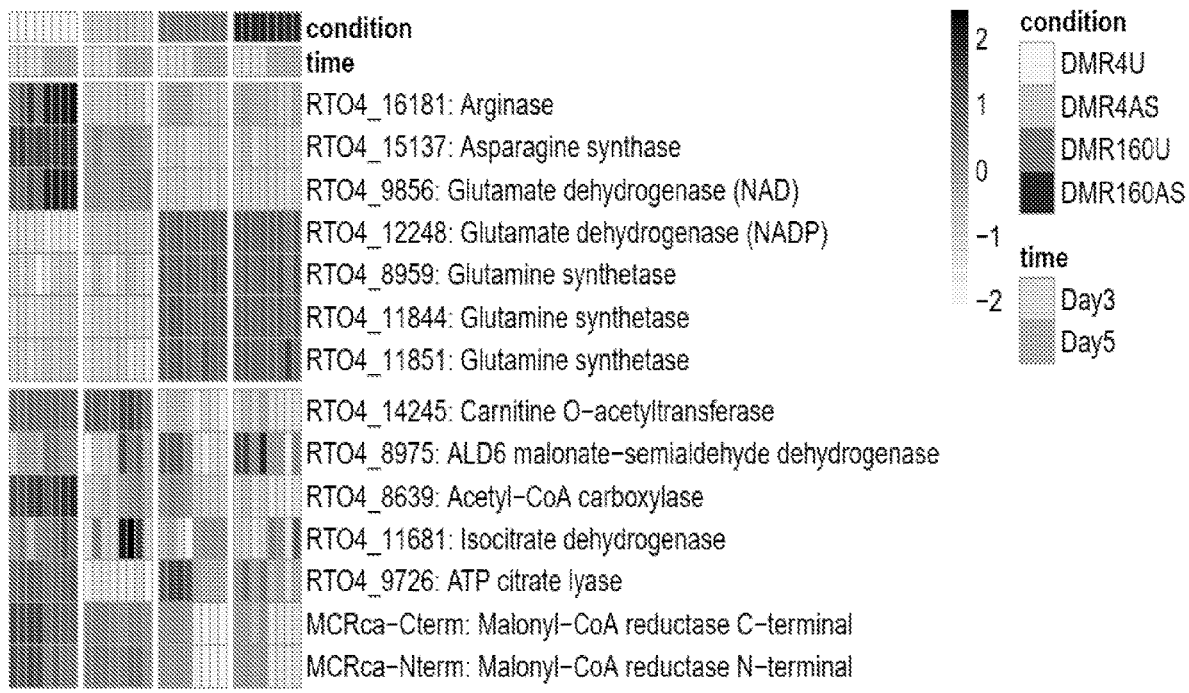
FIGS. 15 and 16 show global proteomic and metabolomic analysis to elucidate shifts in nitrogen metabolism and 3HP pathways. Shading indicates row-wise scaled log 2 abundance.
Figure 16:
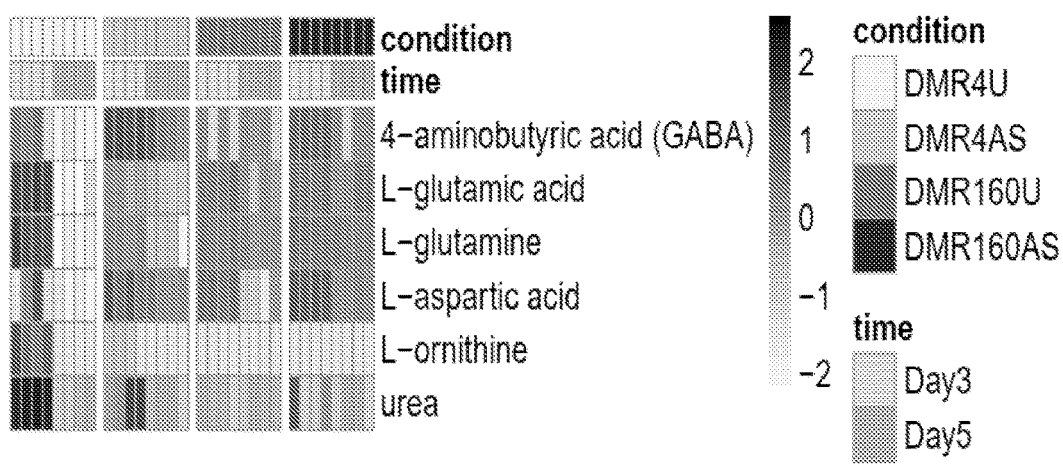

As shown in FIGS. 15 and 16, global proteomic and metabolomic analysis of $MCR_{Ca\text{-}Split}$ in DMR hydrolysate containing urea and ammonium sulfate at two drastically different C:N ratios, 4:1 and 160:1 was performed to gain insights into the metabolic shifts that may lead to increased 3HP production.

Surprisingly different expressions of proteins involved in nitrogen metabolism were observed (See FIG. 15). The expression of arginase, asparagine synthase and glutamate dehydrogenase (NAD-dependent, involved in glutamate degradation) were upregulated in urea media with 4:1 C:N ratio (denoted as DMR4U), whereas glutamine synthetase and glutamate dehydrogenase (NADP-dependent, involved in glutamate biosynthesis) levels were downregulated in both nitrogen sources with 4:1 C:N ratio. Previous studies had shown that in R. toruloides uptake of urea is markedly faster than that of $NH_4^+$ and intracellular $NH_4^+$ can be rapidly released (EVANS and RATLEDGE, 1984, supra), which may have contributed to activation of the nitrogen catabolic enzymes under high urea conditions and accumulation of nitrogen containing metabolites in these pathways. The down-regulation of glutamine synthetase under high nitrogen conditions indicates potential repression of these proteins by $NH_4^+$.

In addition, elevated levels of acetyl-CoA carboxylase in DMR4U media were observed, which have shown to be key to enhancing the precursor of 3HP, malonyl-CoA, in various hosts. Meanwhile, ATP citrate lyase and carnitine o-acetyltransferase levels were both upregulated in DMR4U, which may further contribute to elevated acetyl-CoA levels. It was also interesting to find that the MCR expression levels were slightly higher in DMR4U, which may have also contributed to the enhanced 3HP production under this condition. The expression of ALD6 was also slightly elevated in DMR4U, suggesting potentially more active 3HP catabolism and further motivating knocking out this gene to enhance 3HP production.

Example 13: Combinatorial Strain Engineering to Address 3HP Transport and Catabolism After the two pathway modifications that improve 3HP titers were identified, a next step was to stack these modifications to further improve titers, rates and yields. To this end, the $MCR_{Ca-Split}$ strain with the transporter overexpression under the control of TEF1 promoter (denoted as g2945) was taken and ALD6 was deleted by homologous recombination (strain denoted as ALD6-g2945). To enhance the carbon flux from malonyl-CoA to 3HP, a second copy of $MCR_{Ca-Split}$ was expressed at the ALD6 locus (strain denoted as MCR-ALD6-g2945). These strains were cultured in parallel with the parent strains in a 48-well FlowerPlate in the optimized media conditions as discussed above (DMR8U media).

Figure 17A:
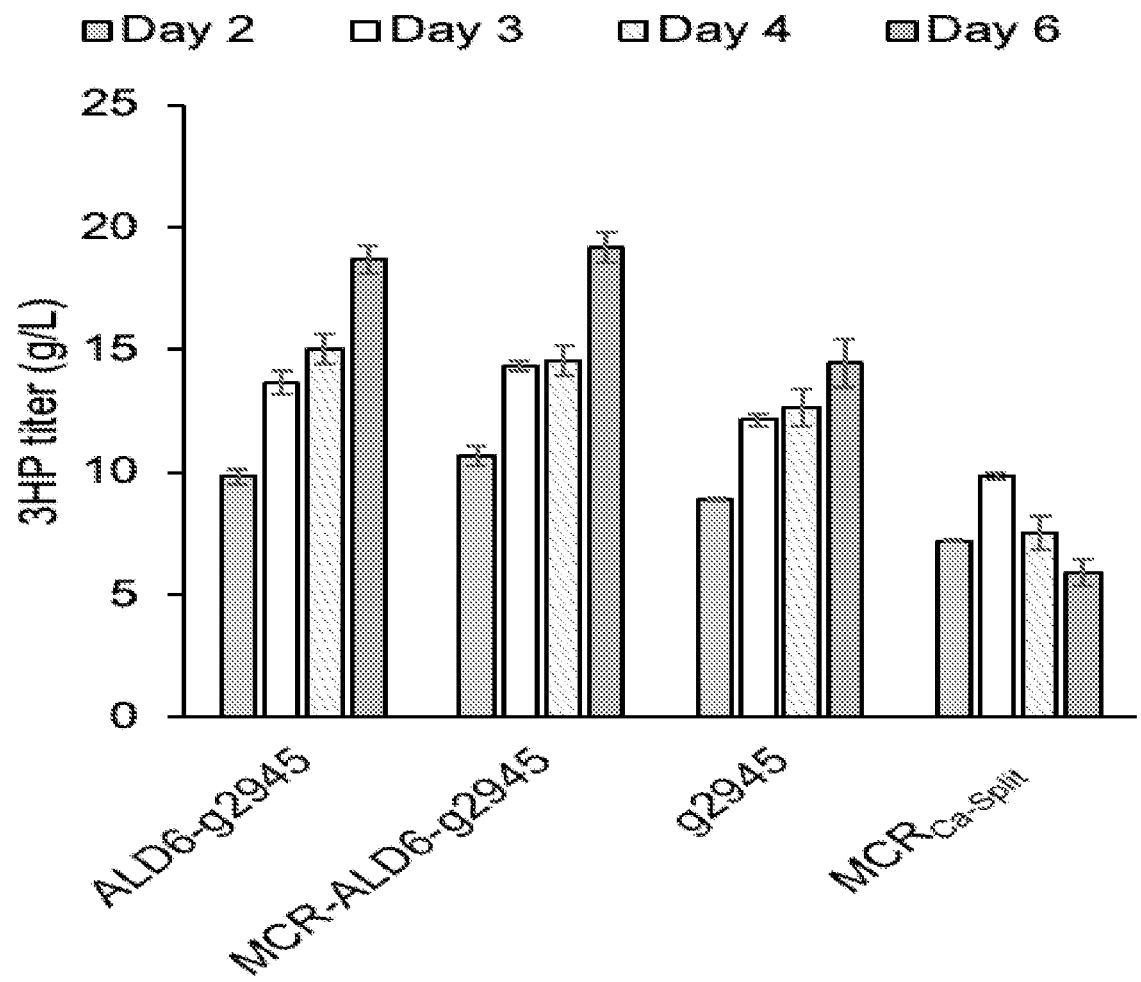
FIGS. 17A to 17C are sets of graphs showing production of 3HP and sugar utilization in engineered *R. toruloides* strains. Error bars represent standard deviations of biological triplicates.
Figure 17B:
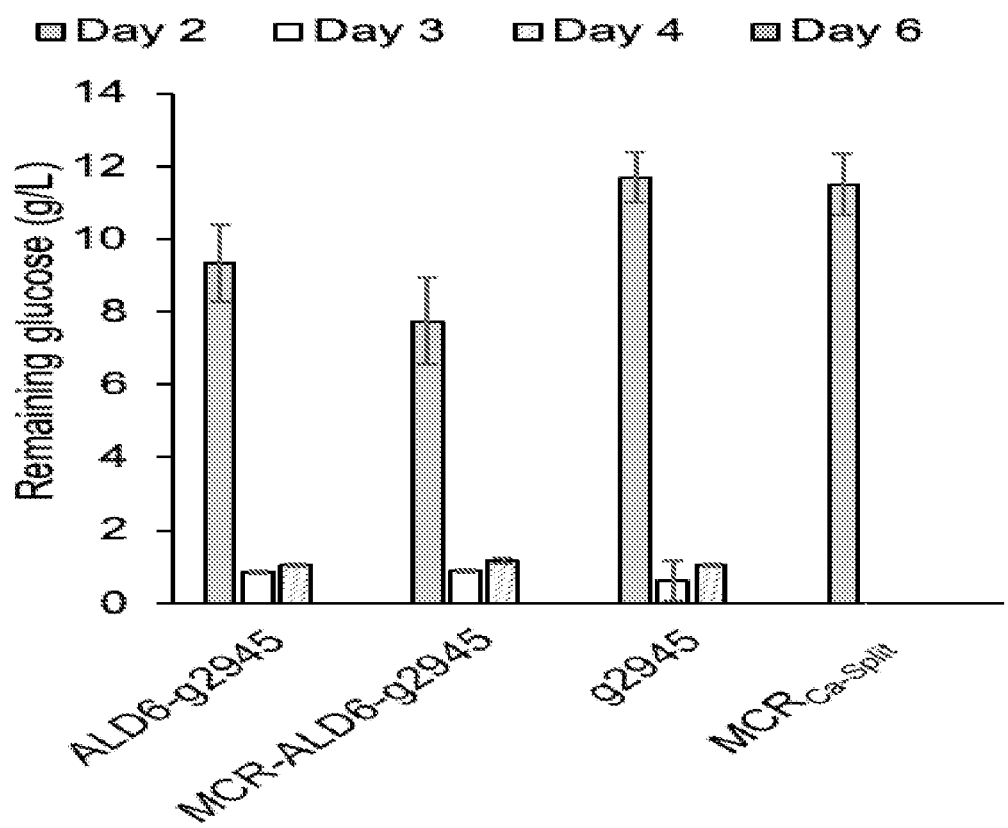
Figure 17C:
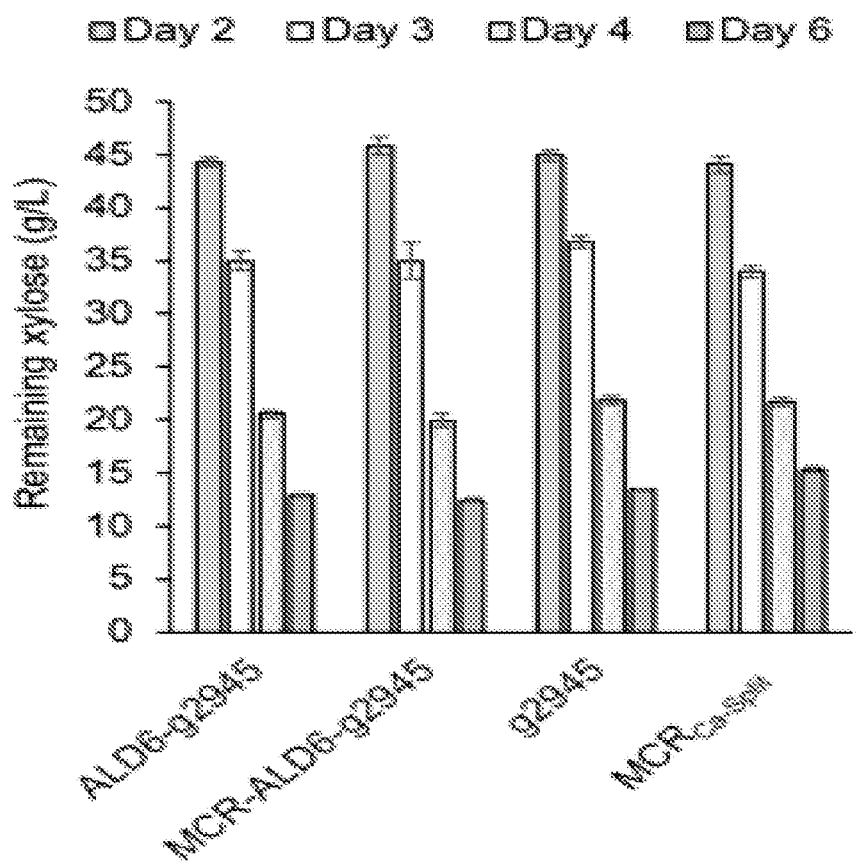

The following strains were cultivated in the DMR8U media for 6 days: g2945, g2945 transporter expression under TEF1 promoter in $MCR_{Ca-Split}$. ALD6-g2945, ALD6 knockout in g2945 strain. MCR-ALD6-g2945, ALD6-g2945 strain with a second copy of $MCR_{Ca-Split}$ expressed at the ALD6 locus. In the $MCR_{Ca-Split}$ strain, 3HP titer peaked at 3 days reaching 9.8 g/L and then dropped (FIG. 17A). The drop is likely due to the active catabolic activities toward 3HP. Compared to $MCR_{Ca-Split}$, the g2945 strain titer increased by 48.0%, reaching 14.5 g/L 3HP at day 6. Although g2945 strain had the 3HP catabolic pathway intact, the transporter actively exports 3HP to the media, thus alleviating the degradation of 3HP. Both ALD6-g2945 and MCR-ALD6-g2945 strains exhibited improved titers compared to the parent g2945 strain, reaching 18.7 g/L and 19.2 g/L, respectively. ALD6-g2945 and MCR-ALD6-g2945 strains showed slightly faster glucose utilization for the first two days, and almost all the glucose was consumed for all the strains after 3 days (FIG. 17B). Xylose utilization started between day 2 and day 3 when glucose levels dropped to close to zero, and the xylose utilization rates did not show any significant differences among the four strains (FIG. 17C).

It was determined that the additional copy of MCR in the MCR-ALD6-g2945 strain did not have any significant impact on 3HP production, indicating that the supply of upstream precursors, i.e. malonyl-CoA, is likely a rate-limiting factor in these strains. Thus, further engineering strategies designed to enhance the pool of precursors in these strains may also be fruitful.

Example 14 Bioreactor Scale-Up of the Combinatorial Strain

Following strain and cultivation condition optimization, further enhancement of 3HP production and demonstration of the feasibility of process scale-up in a 2-L fed-batch bioreactor was sought. The modified DMR8U media was used during the batch fermentation, and glucose was fed manually when glucose level dropped below 20 g/L.

Figure 18A:
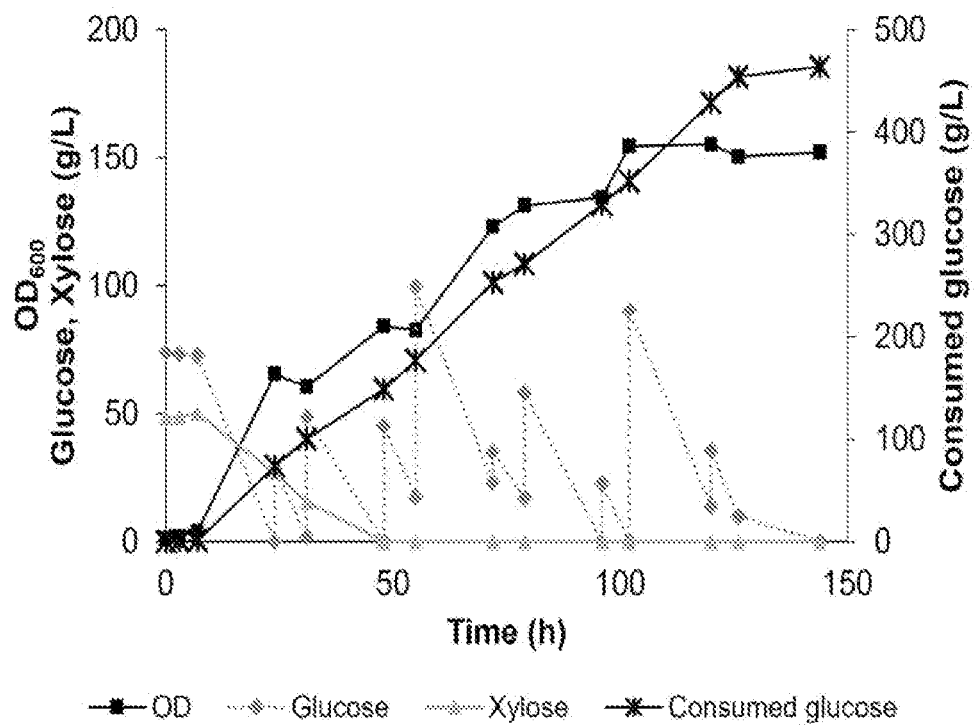
FIGS. 18A and 18B are graphs showing fed-batch fermentation of MCR-ALD6-g2945 strain for 3HP production in a 2 L bioreactor.
Figure 18B:
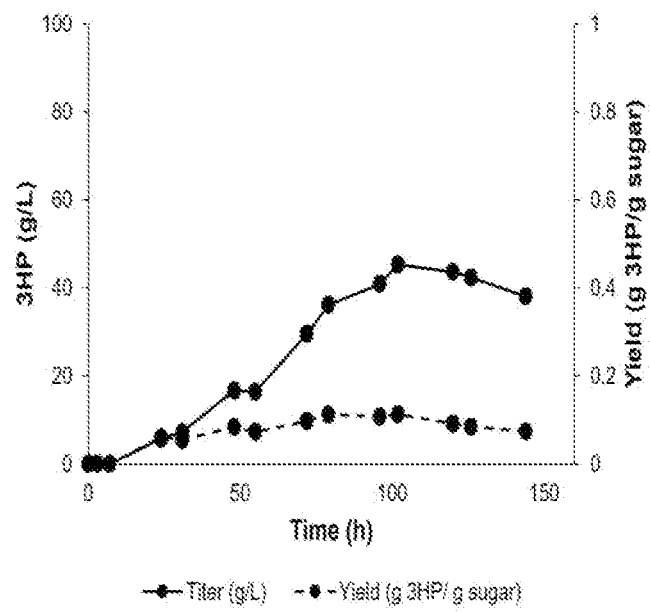

FIGS. 18A and 18B show graphs of fed-batch fermentation of MCR-ALD6-g2945 strain for 3HP production in a 2 L bioreactor. In FIG. 18A, Cell growth, residual concentration of glucose and xylose, and consumed glucose concentrations are shown. In FIG. 18B, 3HP titer and yield are shown.

The maximum cell growth and 3HP production were obtained at 102 hrs, reaching an $OD_{600}$ of 155.2 and 45.4 g/L, respectively. In the first 79 hrs, the strain grew rapidly and reached 86.3% of the maximum cell density. Consistent with observations at the bench-scale, the strain consumed glucose and xylose simultaneously, where the initial glucose was depleted after 22 hrs of cultivation and initial xylose was depleted after 48 hrs. In addition, short periods of reduced cell growth rates and 3HP production (31 hrs, 55 hrs and 96 hrs) were observed during the course of the fermentation. This were likely caused by the low sugar levels at those time points. This suggests further process optimization to maintain higher glucose levels could potentially increase the rates of 3HP production even higher.

A maximum 3HP productivity and yield of 0.44 g/L/h and 0.11 g/g sugars was observed at 102 hrs. Although ALD6 (the protein encoded by RTO4_8975) was knocked out to turn down 3HP catabolism, a drop in 3HP titer towards the end of the fermentation was still observed. This might indicate activation of an alternative 3HP catabolic pathway (such as the reductive pathway, shown in FIG. 1) at late growth phase.

Figure 19:
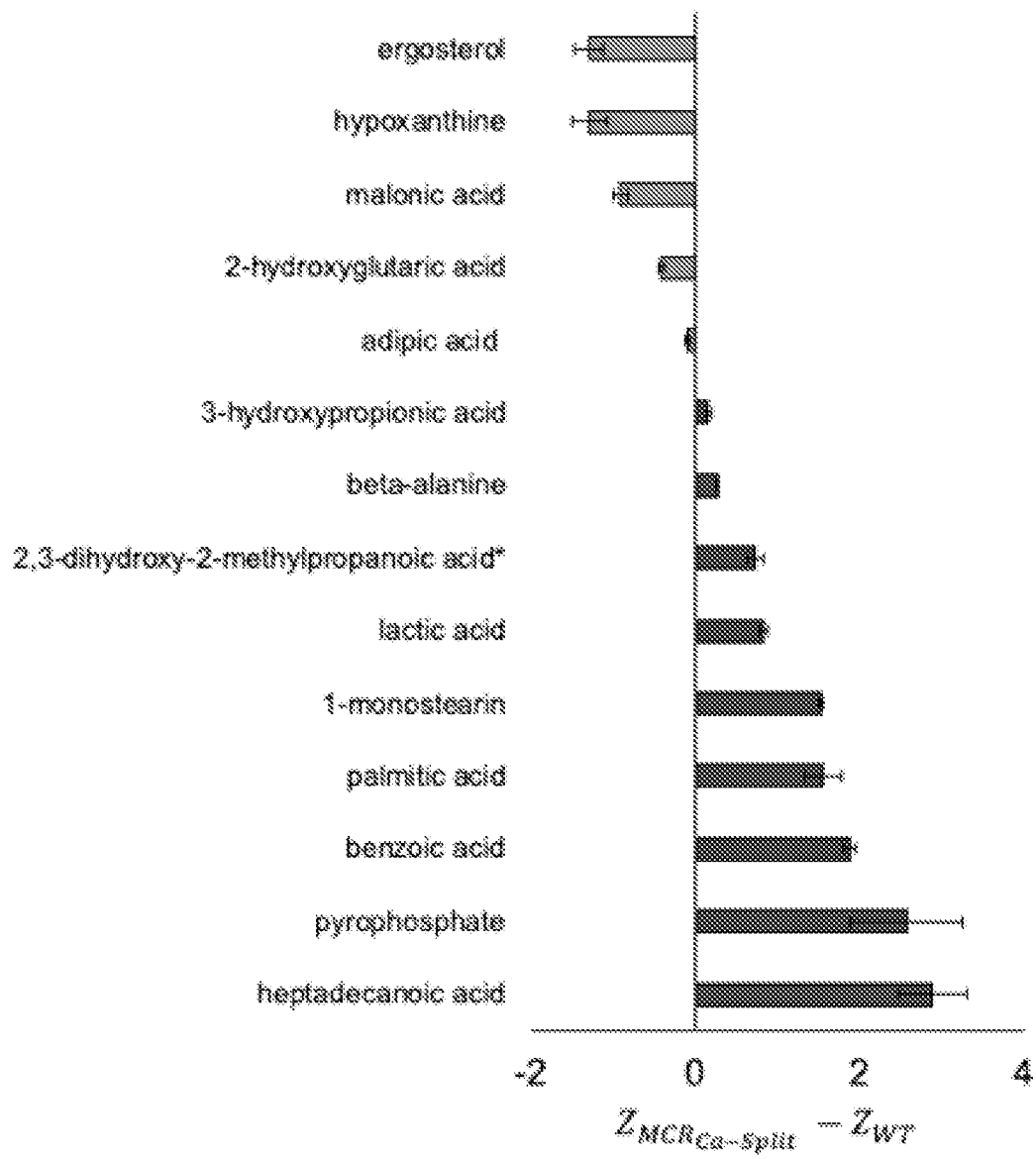
FIG. 19 is a plot showing a difference in Z-scores from differentially accumulated metabolites in $MCR_{Ca-Split}$ at early fermentation stage.

FIG. 19 is a plot showing a difference in Z-scores from differentially accumulated metabolites in $MCR_{Ca-Split}$ at early fermentation stage and the proposed 3HP degradation pathways. $MCR_{Ca-Split}$ and WT *R. toruloides* were cultured in Ambr® 250 and the cell pellets were collected for metabolomic analysis after one day.

All publications, patents, patent applications, and accession number entries mentioned in this specification are incorporated herein by reference to the same extent as if each independent publication or patent application was specifically and individually indicated to be incorporated by reference.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the" should be interpreted to mean "one or more" unless the context indicates the contrary.

It is claimed:

1. An engineered Basidiomycete organism comprising a deletion of a gene comprising at least 90% sequence identity to the nucleotide sequence of SEQ ID NO: 1 in its genome, wherein the Basidiomycete organism is selected from the group consisting of: *Rhodosporidium toruloides, Rhodosporidium azoricum, Rhodosporidium fluviale, Rhodosporidium lusitaniae, Rhodosporidium babievae, Rhodosporidium diobovatum, Rhodosporidium paludigenum, Rhodosporidium sphaerocarpum*, and *Rhodosporidium kratochvilovae*.

2. The engineered Basidiomycete organism of claim 1, wherein the engineered Basidiomycete organism is *R. toruloides*.

3. The engineered Basidiomycete organism of claim 1, wherein the engineered Basidiomycete organism further comprises a transporter comprising the amino acid sequence of SEQ ID NO: 4.

4. The engineered Basidiomycete organism of claim 1, wherein the engineered Basidiomycete organism expresses an Acetyl CoA carboxylase.

5. A fermentation broth composition comprising an energy source comprising glucose and the engineered Basidiomycete organism of claim 1.

6. The fermentation broth composition of claim 5, wherein the engineered Basidiomycete organism is *R. toruloides*.

7. The fermentation broth of claim 5, wherein the engineered Basidiomycete organism further comprises a transporter comprising the amino acid sequence of SEQ ID NO: 4.

8. The fermentation broth of claim 5, wherein the engineered hest Basidiomycete organism expresses an Acetyl CoA carboxylase.

9. The fermentation broth of claim 5, further comprising a urea nitrogen source.

10. The fermentation broth of claim 5, wherein the energy source further comprises a biomass hydrolysate.

11. The fermentation broth of claim 9, wherein a C:N ratio in the fermentation broth is 4:1 to 8:1.

12. A method of producing 3 hydroxypropionic acid, comprising: combining an energy and material source and the engineered Basidiomycete organism of claim 1, thereby producing 3 hydroxypropionic acid.

13. The method of claim 12, further comprising introducing promoter sequences into the Basidiomycete organism to drive monocarboxylate transporter expression for promoting 3HP transport in the engineered host.

14. The method of claim 12, wherein the energy source is a biomass hydrolysate.

15. The method of claim 12, wherein the energy and material source is deacetylated mechanically refined corn stover.

16. The method of claim 12, further comprising overexpressing a transporter comprising the amino acid sequence of SEQ ID NO: 4 in the engineered Basidiomycete organism hest.

17. The method of claim 16, wherein the transporter is expressed under control of pGAPDH promoter, pTEF1 promoter, or both pGAPDH and pTEF1 promoters.

* * * * *

SEQUENCE LISTING

```
Sequence total quantity: 7
SEQ ID NO: 1              moltype = AA  length = 545
FEATURE                   Location/Qualifiers
REGION                    1..545
                          note = Synthetic: RT04_8975
source                    1..545
                          mol_type = protein
                          organism = synthetic construct
SEQUENCE: 1
MLSHTLRTSG SLRTLATRRT FTTTPARRAL ADLEALAATH PWSGTATDGQ RATTHLIGGE    60
YTTGDSTHWI DVHDPSTQRV LTRVPESTPQ VLKRAVDKAE EAFDEWKDSS ILKRQAVMLK   120
FQSLIREHHD EIARSIVLEQ GKTFADAKGD VLRGLQVVEN ACGIPSLLLA DKLEVSKDMD   180
TFVRKVPLGV TAAVCPFNFP AMIPLWAMGM SIACGNSLIL KPSERDPGAT MILAELLEQA   240
GLPKGVLQVV HGTIAPVKFI CEEPRIKAIS FVGGDKAGQY IYETGSKNGK RVQANLGAKN   300
HCILMPDANA NFALNSIVGA AFGAAGQRCM ALSTLVAVGE SQTWIDGLVE RAKKLKVGNG   360
FDPETEVGPL ITPAAKERVE SLIQSCADQG GKILLDGRGA KPKGYEKGNF VGPTILEATT   420
DMDCYTQEIF GPVLTIVKAD TLDDAIALIN RNRYGNGSSV FTNSGATARR FEKEIQAGQV   480
GINVPIPVPL PMFSWSGNKG SVLGGASLYG PRGVDFWTQN KTVTSYWRAE DAIDTRATTA   540
MPTHH                                                               545

SEQ ID NO: 2              moltype = DNA  length = 1650
FEATURE                   Location/Qualifiers
misc_feature              1..1650
                          note = Synthetic: MCRCA-NTERM
source                    1..1650
                          mol_type = other DNA
                          organism = synthetic construct
SEQUENCE: 2
atgtcgggca cggccgcct cgcgggcaag atcgcgctca tcacgggcgg cgcgggcaac     60
atcggctcgg agctcacgcg ccgcttcctc gcggagggcg cgacggtcat catctcgggc   120
cgcaaccgcg cgaagctcac ggcgctcgcg gagcgcatgc aggcggaggc gggcgtcccg   180
gcgaagctca tcgacctcga ggtcatggac ggctcgggac ccgtcgcggt ccgcgcgggc   240
atcgaggcga tcgtcgcgcg ccacggccag atcgacatcc tcgtcaacaa cgcgggctcg   300
gcgggcgcgc agccgcgcct cgcggagatc ccgctcacgg aggcggagct cggcccgggc   360
gcggaggaga cgctccacgc gtcgatcgcg aacctcctcg gcatgggctg gcacctcatg   420
cgcatcgcgg cgccgcacat gccggtcggc tcggcgtcga tcaacgtctc gacgatcttc   480
tcgcgcgcgg agtactacgg ccgcatcccg tacgtcacgc cgaaggcggc gctcaacgcg   540
ctctcgcagc tcgcggcgcg cgagctcggc gcgcgcggca tccgcgtcaa cacgatcttc   600
ccgggcccga tcgagtcgga ccgcatccgc acggtcttcc agcgcatgga ccagctcaag   660
ggccgccggg agggcgacac ggcgcaccac ttcctcaaca cgatgcgcct ctgccgcgcg   720
aacgaccagg gcgcgctcga gcgccgcttc ccgtcggtcg gcgacgtcgc ggacgcgggc   780
gtcttcctcg cgtcggcgga gtcggcggcg ctctcgggcg agacgatcga ggtcacgcac   840
ggcatggagc tcccggcgtg ctcggagacg tcgctcctcg cgcgcacgga cctccgcacg   900
atcgacgcgt cgggccgcac gacgctcatc tgcgcgggcg accagatcga ggaggtcatg   960
gcgctcacgg gcatgctccg cacgtgcggc tcggaggtca tcatcggctt ccgctcggcg  1020
gcggcgctcg cgcagttcga gcaggcggtc aacgagtcgc gccgcctcgc gggcgcggac  1080
ttcacgccgc cgatcgcgct cccgctcgac ccgcgcgacc cggcgacgat cgacgcggtc  1140
ttcgactggg cgggcgagaa cacgggcggc atccacgcgg cggtcatcct cccggcgacg  1200
tcgcacgagc cggcgccgtg cgtcatcgag gtcgacgacg agcgcgtcct caacttcctc  1260
gcggacgaga tcacgggcac gatcgtcatc gcgtcgcgcc tcgcgcgcta ctggcagtcg  1320
cagcgcctca cgccgggcgc gcgcgcgcgc ggcccgcgcg tcatcttcct ctcgaacggc  1380
gcggaccaga acggcaacgt ctacggccgc atccagtcgg cggcgatcgg ccagctcatc  1440
cgcgtctggc gccacgaggc ggagctcgac taccagcgcg cgtcggcggc gggcgaccac  1500
gtcctcccgc cggtctgggc gaaccagatc gtccgcttcg cgaaccgctc gctcgagggc  1560
ctcgagttcg cgtgcgcgtg gacggcgcag ctcctccact cgcagcgcca catcaacgag  1620
atcacgctca acatcccggc gaacatctaa                                   1650

SEQ ID NO: 3              moltype = DNA  length = 2016
FEATURE                   Location/Qualifiers
misc_feature              1..2016
                          note = Synthetic: MCRCA-CTERM
source                    1..2016
                          mol_type = other DNA
                          organism = synthetic construct
SEQUENCE: 3
atgtcggcga cgacgggcgc gcgctcggcg tcggtcggct gggcggagtc gctcatcggc    60
ctccacctcg gcaaggtcgc gctcatcacg gcggcgctcg gcggcatcgg cggccagatc   120
ggccgcctcc tcgcgctctc gggcgcgcgc gtcatgctcg cggcgcgcga ccgccacaag   180
ctcgagcaga tgcaggcgat gatccagtcg gagctcggcg aggtcggcta cacggacgtc   240
gaggaccgcg tccacatcgc gccgggctgc gacgtctcgt cggaggcgca gctcgcggac   300
ctcgtcgagc gcacgctctc ggcgttcggc acggtcgact acctcatcaa caacgcgggc   360
atcgcgggcc tcgaggagat ggtcatcgac atgccggtcg agggctggcg ccacacgctc   420
ttcgcgaacc tcatctcgaa ctactcgctc atgcgcaagc tcctcccgct catgaagaag   480
cagggctcgg gctacatcct caacgtctcg tcgtacttcg gcggcgagaa ggacgcgagc   540
atcccgtacc cgaaccgcgc ggactacgcg gtctcgaagg cgggccagcg ccgcgatggc   600
gaggtcttcg cgcgcttcct cggccgcgag atccagatca acgcgatcgc gccgggcccc   660
gtcgagggcg accgcctccg cggcacgggc gagcgcccgg gcctcttcgc gcgccgcgcg   720
cgcctcatcc tcgagaacaa gcgcctcaac gagctccacg cggcgctcat cgcggcgcgg   780
```

```
cgcacggacg agcgctcgat gcacgagctc gtcgagctcc tcctcccgaa cgacgtcgcg   840
gcgctcgagc agaacccggc ggcgccgacg gcgctccgcg agctcgcgcg ccgcttccgc   900
tcggagggcg accggcggc gtcgtcgtcg tcggcgctcc tcaaccgctc gatcgcggcg   960
aagctcctcg cgcgcctcca caacggcggc tacgtcctcc cggcggacat cttcgcgaac  1020
ctcccgaacc cgccggaccc gttcttcacg cgcgcgcaga tcgaccgcga ggcgcgcaag  1080
gtccgcgacg gcatcatggg catgctctac ctccagcgca tgccgacgga gttcgacgtc  1140
gcgatggcga cggtctacta cctcgcggac cgcaacgtct cgggcgagac gttccacccg  1200
tcgggcggcc tccgctacga gcgcacgccg acgggcggcg agctcttcgg cctcccgtcg  1260
ccggagcgcc tcgcggagct cgtcggctcg acggtctacc tcatcggcga gcacctcacg  1320
gagcacctca acctcctcgc gcgcgtac ctcgagcgct acggcgcgcg ccaggtcgtc  1380
atgatcgtcg agacggagac gggcgcggag acgatcgcgc gcctcctcca cgaccacgtc  1440
gaggcgggcc gcctcatgac gatcgtcgcg ggcgaccaga tcgaggcggc gatcgaccag  1500
gcgatcacgc gctacggccg cccggggcccg gtcgtctgca cgccgttccg cccgctcccg  1560
acggtcccgc tcgtcggccg caaggactcg gactggtcga cggtcctctc cgagggcgag  1620
ttcgcggagc tctgcgagca ccagctcacg caccacttcc gctcgcgcg caagatcgcg  1680
ctctcggacg gcgcgtcgct cgcgctcgtc acgccggaga cgacggcgac gtcgacgacg  1740
gagcagttcg cgctcgcgaa cttcatcaag acgacgctcc acgcgttcac ggcgacgatc  1800
ggcgtcgagt cggagcgcac ggcgcagcgc atcctcatca accaggtcga cctcacgcgc  1860
cgcgcgcgcg cggaggagcc gcgcgacccg cacgagcgcc agcaggagct cgagcgcttc  1920
atcgaggcgg tcctcctcgt cacggcgccg ctcccgccgg aggcggacac gcgctacgcg  1980
ggccgcatcc accgcggccg cgcgatcacg gtctaa                            2016
```

| SEQ ID NO: 4 | moltype = AA   length = 418 |
|---|---|
| FEATURE | Location/Qualifiers |
| REGION | 1..418 |
| | note = Synthetic: PROTEIN SEQUENCE OF G2945 (3HP TRANSPORTER) |
| source | 1..418 |
| | mol_type = protein |
| | organism = synthetic construct |

SEQUENCE: 4
```
MPSNTRVASI SHGSDFSLSL PPDGGARAWT QVLCMHFVFF NTWGVSNSFS VYQQLYTASF    60
TQSASEISWI GSVQVFLLFF IGVLAGRATD AGYFRPVYMA GVLLQLVGIF MLSLCKTYWQ   120
VFLAQAVCMG LGNGLVFTPG LSVMSSYFEK NRAFAVGLAS SGAATGGMVY PVVVNQLLYT   180
HSIGFAWTTR AAGLVMLLTH LPGLVLFRPR LPPRTTGPLI DWEAFTERPF VFITLSMFLN   240
FWGLYFAFFY LGTFARDRIG IEHTQNLVLV LNGVGVVGRI VPTLIGDRVL GRLNTLIPSS   300
LASSLLIYCW IPVSTQGGLY AFAAVYGVVG GAAQALFPAS ITTMSPDIKK TGTRVGMILS   360
IVSIATLTGP AIEGALIHRA GGSYLYAQIF AATSILVGAF AAIAARIAKT GWAWNVKA    418
```

| SEQ ID NO: 5 | moltype = DNA   length = 1429 |
|---|---|
| FEATURE | Location/Qualifiers |
| misc_feature | 1..1429 |
| | note = Synthetic: PROMOTER SEQUENCE OF GAPDH |
| source | 1..1429 |
| | mol_type = other DNA |
| | organism = synthetic construct |

SEQUENCE: 5
```
ctgcagaact acgccctctc acacccaact tccgactcga ccggcggtac gagcacgacc    60
tacttctact gcctgccatc gacatccggg cgggtcgctg cctaccctgt gcgttctgcg   120
ccctccctcg tctcggggagg cagtgtctga cagaagcttt gcgcgcagta ccccgtcaag   180
atgcaactct acgcaacgtt cggcacagaa gtcgccaatc tccgcgcatc gccgcctcaa   240
gctctcgcgc tgcccgacgg tgtcgtctat tacgaggcgg agaagctcga gttgccggct   300
ttgccagcgg cggtcaaggt tgaggtggag acggagaagg cgggagtagc gggggaggac   360
aatgaggcga agggtgagat ggtgctggtg gagactcttc cggtggagca ggaggagatt   420
gaattgggct cgggagtcgt gcagattgag gagtcgttgc tcgtcaagct ggaggtcagc   480
ggctgatcct tccgttcgtt gcaaggatcg tctgcatgtt tcgcttctct caatgacaca   540
acctggagag cgctcccgtc agcgagaatc gaggacattc gcagctcgt gagcaagcgg   600
aggtgcgagg ctccctcgaa agctgcgcct cttcagacgg cttgttctct cctgctctgg   660
tgggctggcc tgacatgtaa tgtgctccgc cgcaagtccg tcgtcggtct caattcgaac   720
ttgaaagggc atagcgcaag gaagaaccct ctgcggacat gcagaattac tggctcgcct   780
gctccttcgt ctactggaat aagtcctgtc tcgttaaagc cccaacgtcg ttttttcgacg   840
tttgtaaggc gcaagaggtg ctatgggcta cgcaggaagc tgagaggaca tagaagtcgg   900
gggaggaacg gcgcagagcg gcagttgcgg aagcatgagg aaagcgagac ggtccagcat   960
ctgcagcgcc aatccgcaat ctcctggttg agcctgcacc ggaagcgtcg gaacagtatg  1020
cgcagagtcg aacgcaagta agaaagacgc accctcacac tcgcttactt cgagccatac  1080
aacggatcaa agctgcgcgt atctcggctt gtaagggccg gaaagcaacc tcggagatgg  1140
acacgtcaca tcaccaactt atcgatctcg gccgtcgacg tcgcagagag ggcgagagaa  1200
gcggtgaagg agggaaacaa cccctcgaga gcatgatccg accgaatctg cagcgcagga  1260
agccgttaca agcccgcctc gagcgcaggt cgggtccagc cggggccaga aacgcgcaga  1320
gctgattcgt gagcgaagga agccgcatcg acaagttcgc tccccttgc cctctttccc  1380
atcacccgtt ctcgccttac ccgctcagaa caacaccaga tcactcaca              1429
```

| SEQ ID NO: 6 | moltype = DNA   length = 946 |
|---|---|
| FEATURE | Location/Qualifiers |
| misc_feature | 1..946 |
| | note = Synthetic: PROMOTER SEQUENCE OF TEF1 |
| source | 1..946 |
| | mol_type = other DNA |
| | organism = synthetic construct |

```
SEQUENCE: 6
catgctgctg ctgccctca aaggtcctct cgtccacgtc cgacgagtct ggacagcttt      60
cacagtcccg agagtgcaag agcgaggcgg gctcacggtt ccgcaaagga gcgcgaggtc    120
cgaccgccgg ccggtctcct tgcccgcctc gcctcacctc ctcttgcagc aggttcacct    180
cttcgaggtc actcgatcgc tcgcagcgat gcgcaggtac aagtacgcta ggcgagagcg    240
tcgaaagcgg ggttctgcga gggactggac gctgcagagc gcggtcgaga gaggctcgag    300
tggcgctttg accgctcgac gcaaggcatg cgctcctccg tttgagctcg cagatactgc    360
cgtgcgaaga cgagcatagg ctgtggctgc ggtagcaagg agccggcgag agaaagctgt    420
gctcgagcag gacgagagac ggtccgcgcg cttgagaagg tcgaggtgag gcgtcgcaac    480
cgggttggat ctcgattctc ggcgaactac ggcttcggcg agggccaaag cgacggcagg    540
ccgcgcaagc tggccaggcg agagcgcgag agtcgcgagc tgaagcgggc gcggggtaga    600
gcaagctggg gaagcgagag agggagagag agagagtgag ggggtggcga ggtggagacg    660
aggcgagcgg ttggcttgcg cgcgcgcgag agggatcgag gcgagaggcg agccccgaga    720
gtggaaggaa ggacgaggaa acctgcgtgc ggaggcgccg cgcgccgcgtg ccacctggct   780
gagcacgggc ccgagcttga gggagctggg ggcgcgcgag cgagacgagg gcagggcgag    840
cccgcgcgtg gcggccgcct cgcaacccaa ggctcgccct ggccgccgct cttgctctct    900
ttcctccacc ttcgcgtctc accactcgaa tctcacttca tccatc                  946

SEQ ID NO: 7            moltype = DNA   length = 451
FEATURE                 Location/Qualifiers
misc_feature            1..451
                        note = Synthetic: Promoter sequence of P9 that controls
                        MCRCa-Split
source                  1..451
                        mol_type = other DNA
                        organism = synthetic construct
SEQUENCE: 7
gttctgtagg agagggttgg taggttgtga gggtggtgtg agggtgcggg taaccgggaa     60
gtgttcggac gggtgggaag gaaggagagg gacgacgagc ctgcgcgacg aggttgatcg    120
accgcgcgcg cgccaaacaa tcaataccta ggctcgtgcc tctgttacta ggtcaacagt    180
aagcctagtt atgcgtacat ccgcatcaat tctcgtacgc accttctaga gctgggcaaa    240
caaagccact tcccgcgcgc ctcatagctc gtccttcgcc acgctcctct ctctcccttc    300
ttcccaccac cttcagcaca ccggcctcgc cgtctcgaca cgctcctctc ctcacctcaa    360
cccccaacaa cacctcaatc aaacagtgcg tcccgtccag ctcaaacagc gaccgagccg    420
agctgaccdt gtcccgcact tcccgcaaca g                                   451
```